United States Patent
Oddou et al.

(10) Patent No.: US 8,172,781 B2
(45) Date of Patent: *May 8, 2012

(54) ORTHOPEDIC BRACE HAVING A LENGTH-ADJUSTING MECHANISM AND A LOCKABLE ROTATION HINGE

(75) Inventors: Paul Oddou, Salt Lake City, UT (US); Dylann D. Ceriani, San Diego, CA (US); James D. Burke, Encinitas, CA (US); Jeffrey T. Mason, Escondido, CA (US)

(73) Assignee: Breg, Inc., Carlsbad, CA (US)

( * ) Notice: Subject to any disclaimer, the term of this patent is extended or adjusted under 35 U.S.C. 154(b) by 90 days.

This patent is subject to a terminal disclaimer.

(21) Appl. No.: 12/750,646

(22) Filed: Mar. 30, 2010

(65) Prior Publication Data

US 2011/0082402 A1 Apr. 7, 2011

Related U.S. Application Data

(63) Continuation of application No. 11/039,056, filed on Jan. 12, 2005.

(51) Int. Cl.
  *A61F 5/37* (2006.01)
  *A61F 5/00* (2006.01)
  *A61F 13/00* (2006.01)
  *A61F 13/06* (2006.01)
  *A61B 19/00* (2006.01)

(52) U.S. Cl. .................. 602/26; 602/5; 602/12; 602/16; 602/23; 602/60; 602/61; 602/62; 128/846; 128/869; 128/882

(58) Field of Classification Search ................ 602/5, 12, 602/16, 23–26, 60–62; 128/846, 869, 882, 128/898

See application file for complete search history.

(56) References Cited

U.S. PATENT DOCUMENTS

| 401,933 | A | 4/1889 | De Camp |
| 552,143 | A | 12/1895 | Rankin |
| 649,237 | A | 5/1900 | Dyson |
| 2,812,961 | A | 11/1957 | Brown et al. |
| 2,853,999 | A | 9/1958 | Risser |
| 3,439,672 | A | 4/1969 | Fisher |
| 3,805,773 | A | 4/1974 | Schau |
| 4,481,941 | A | 11/1984 | Rolfes |
| 4,489,718 | A | 12/1984 | Martin |
| 4,531,515 | A | 7/1985 | Rolfes |
| 4,620,532 | A | 11/1986 | Houswerth |
| 4,655,201 | A | 4/1987 | Pirmantgen |

(Continued)

FOREIGN PATENT DOCUMENTS

WO 02/02035 A1 10/2002

*Primary Examiner* — Patricia Bianco
*Assistant Examiner* — Brandon Jackson
(74) *Attorney, Agent, or Firm* — Rodney F. Brown

(57) ABSTRACT

An orthopedic brace is provided with an adjustable support assembly having a support arm, a housing and a locking mechanism. The housing includes a travel track which slidably receives the support arm. The locking mechanism includes a lock lever which selectively applies a sufficient force to the support arm to prevent slidable displacement of the support arm in the travel track. The orthopedic brace is further provided with a hinge having a first rotation plate, a second rotation plate, a pivotal connector connecting the first and second rotation plates, a rotation limiting mechanism, and a rotation locking mechanism.

17 Claims, 18 Drawing Sheets

U.S. PATENT DOCUMENTS

| | | | |
|---|---|---|---|
| 4,776,326 A | 10/1988 | Young et al. |
| 4,817,588 A | 4/1989 | Bledsoe |
| 4,982,732 A | 1/1991 | Morris |
| 5,000,169 A | 3/1991 | Swicegood et al. |
| 5,018,514 A | 5/1991 | Grood et al. |
| 5,052,379 A | 10/1991 | Airy et al. |
| 5,062,858 A | 11/1991 | Broeck et al. |
| 5,138,911 A | 8/1992 | Lan |
| 5,292,303 A | 3/1994 | Bastyr et al. |
| 5,409,449 A | 4/1995 | Nebolon |
| 5,425,700 A | 6/1995 | Aaserude et al. |
| 5,443,444 A | 8/1995 | Pruyssers |
| 5,460,599 A | 10/1995 | Davis et al. |
| 5,621,953 A | 4/1997 | Fildan |
| 5,653,680 A | 8/1997 | Cruz |
| 5,658,241 A | 8/1997 | Deharde et al. |
| 5,658,243 A | 8/1997 | Miller et al. |
| 5,672,152 A | 9/1997 | Mason et al. |
| 5,814,000 A | 9/1998 | Kilbey |
| 5,817,040 A | 10/1998 | Hess et al. |
| 5,827,208 A | 10/1998 | Mason et al. |
| 5,921,946 A | 7/1999 | Tillinghast et al. |
| 5,938,629 A | 8/1999 | Bloedau |
| 6,347,817 B1 | 2/2002 | Chou |
| 6,381,810 B2 | 5/2002 | Hsieh |
| 6,383,156 B1 | 5/2002 | Enzerink et al. |
| 6,553,572 B2 | 4/2003 | Fiorini et al. |
| 6,560,825 B2 | 5/2003 | Maciejczyk |
| 6,669,659 B2 | 12/2003 | Dittmer et al. |
| 6,735,826 B2 | 5/2004 | Uehara et al. |
| 6,789,296 B2 | 9/2004 | Yang |
| 6,821,261 B2 | 11/2004 | Doty et al. |
| 6,868,585 B2 | 3/2005 | Anthony et al. |
| 6,912,729 B2 | 7/2005 | Nishimoto |
| 6,926,685 B1 | 8/2005 | Modglin |
| 6,981,957 B2 | 1/2006 | Knecht et al. |
| 6,993,808 B1 | 2/2006 | Bennett et al. |
| 7,022,094 B2 | 4/2006 | Buckman et al. |
| 7,037,287 B2 | 5/2006 | Cormier et al. |
| 7,083,583 B2 | 8/2006 | Ophale et al. |
| 7,097,627 B2 | 8/2006 | Enzerink et al. |
| 7,128,723 B2 | 10/2006 | Doty et al. |
| 7,235,059 B2 | 6/2007 | Mason et al. |
| 2005/0070831 A1* | 3/2005 | Cormier et al. ............ 602/26 |

* cited by examiner

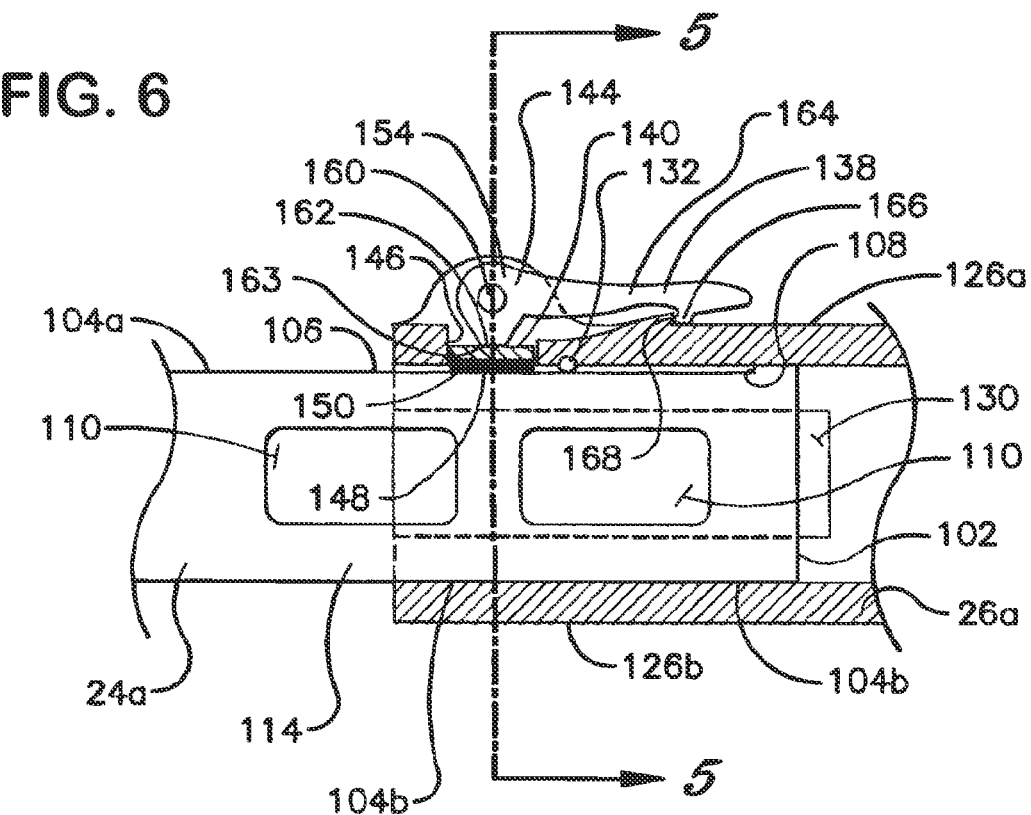
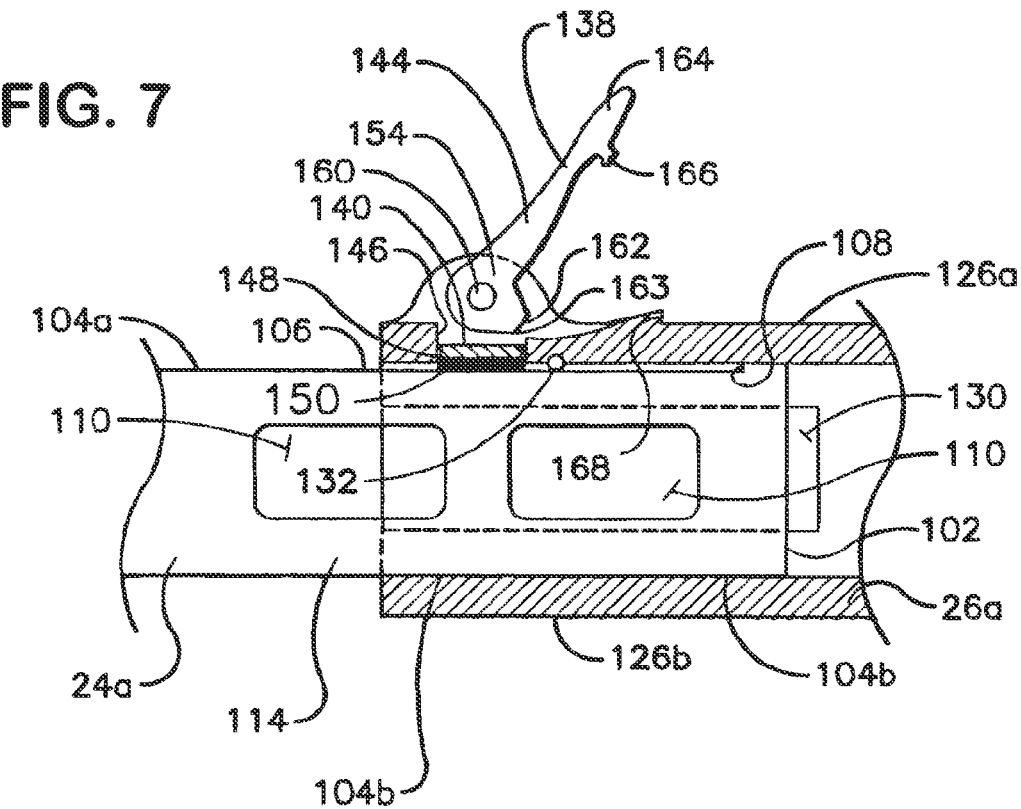

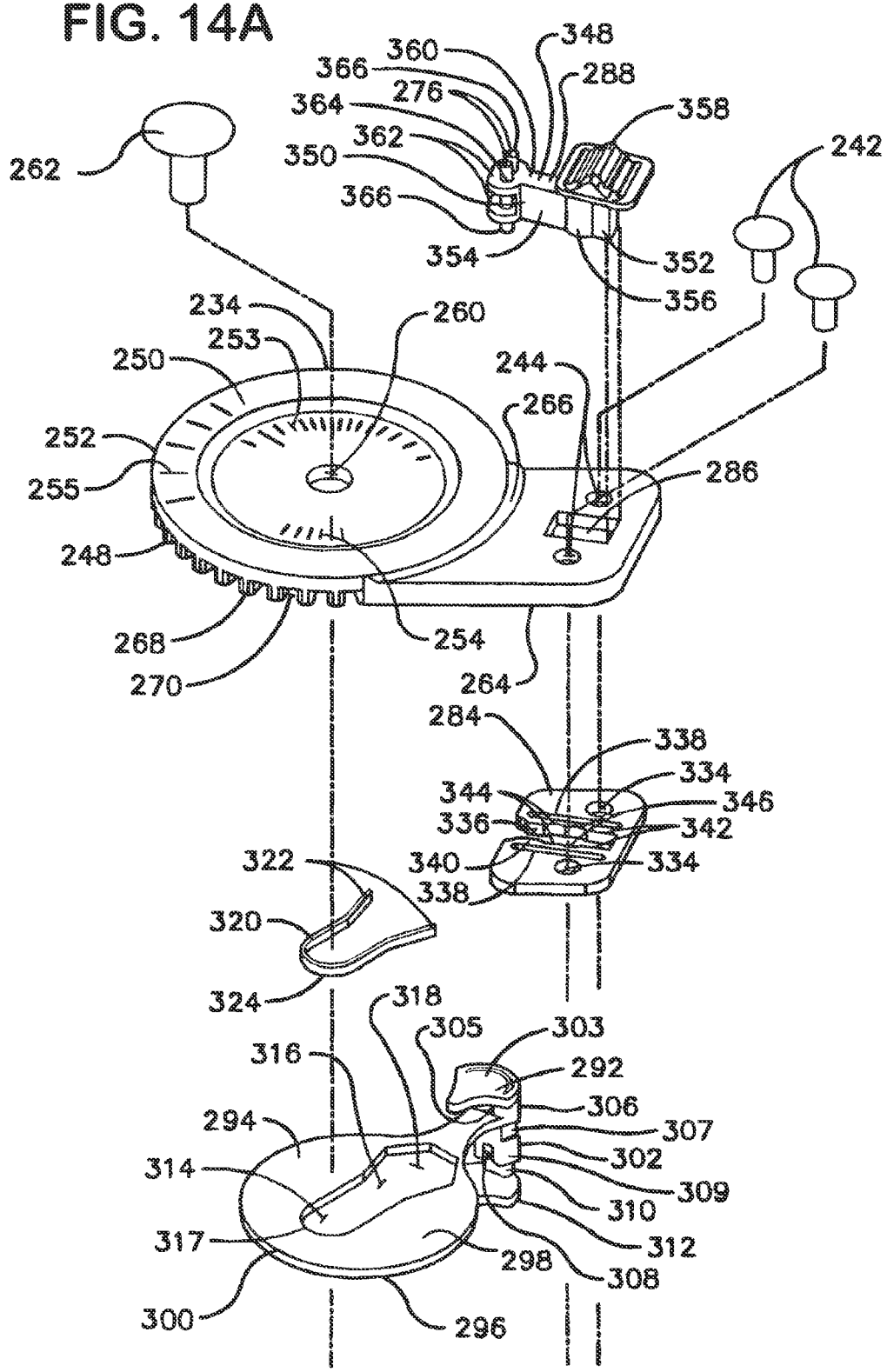

ORTHOPEDIC BRACE HAVING A LENGTH-ADJUSTING MECHANISM AND A LOCKABLE ROTATION HINGE

This application is a continuation of prior application Ser. No. 11/039,056 filed on Jan. 12, 2005 and published on Jul. 13, 2006 as U.S. Patent Application Publication No. 2006/0155229 A1.

TECHNICAL FIELD

The present invention relates generally to orthopedic braces, and more particularly to an orthopedic brace having a length-adjusting mechanism and a lockable rotation hinge.

BACKGROUND OF THE INVENTION

Orthopedic braces are worn on the body of a user either to support a healthy skeletal joint that is at risk of injury or to stabilize a skeletal joint that has been destabilized by an injury or other condition. Orthopedic braces generally include rigid structural components to support or stabilize the skeletal joint. Frequently, although not necessarily, the rigid structural components are dynamically linked together by one or more hinges enabling controlled pivotal movement of the skeletal joint during user activity or rehabilitative therapy. The orthopedic brace is positioned on the body such that the hinges traverse the skeletal joint, while the rigid components are secured to the body above and below the skeletal joint.

Hinges for orthopedic braces having an adjustable rotation range in the extension and flexion direction are well known in the art. For example, U.S. Pat. No. 4,481,941 to Rolfes discloses a hinge having a pair of threaded screws, each being selectively threadably securable in one of a plurality of correspondingly threaded holes formed in the body of the hinge. The hinge rotation range is a function of screw placement insofar as securing a screw in a given hole determines a particular hinge rotation limit. The hinge rotation range is adjusted by changing the hinge rotation limit, which requires removal of the screw from its respective hole and placement of the screw in an alternate hole. However, It has been found that the task of adjusting the hinge rotation range can require a significant degree of dexterity to maneuver the relatively small screws into and out of the threaded holes. Furthermore, the screws are susceptible to being misplaced or lost during this task.

An alternate adjustable hinge disclosed by U.S. Pat. No. 401,933 to De Camp, substitutes pins for threaded screws as a means for setting the hinge rotation limit. The smooth surface of the pins enables them to slide in and out of the holes formed in the body of the hinge. The pins are secured in the holes by a leaf spring attached to each pin which biases the pin into its respective hole in a direction parallel to the axis of hinge rotation. Repositioning the pins of De Camp requires less dexterity than repositioning the screws of Rolfes. Nevertheless, De Camp still requires the user to pry the leaf spring away from the hinge body and remove the pin from the hole when adjusting the hinge rotation range. Accordingly, hinges having an improved adjustment mechanism were developed and disclosed in U.S. Pat. Nos. 5,672,152 and 5,827,208 to Mason et al.

The hinges of Mason et al. are relatively easy to set at a desired rotation limit in the extension or flexion direction and also have the desirable capability of being selectively lockable against rotation altogether. In accordance with one embodiment, the hinge of Mason et al. includes a plurality of rotation limiting notches and a locking notch formed in the peripheral edge of the hinge. A rotation limiting assembly is provided which is selectively positionable in one of the rotation limiting notches to define a hinge rotation limit. Alternatively, the rotation limiting assembly is selectively positionable in the locking notch to lock the hinge against rotation. The hinge also includes a biasing assembly which biases the rotation limiting assembly in a radially inward direction perpendicular to the axis of hinge rotation, thereby retaining the rotation limiting assembly in its selected rotation limiting position or locked position. The biasing assembly, however, enables elastic radial displacement of the rotation limiting assembly in a radially outward direction when a radially outward displacement force is externally applied thereto. The biasing assembly returns the rotation limiting assembly to a selected rotation limiting or locked position when the displacement force is withdrawn.

Although the above-recited hinge of Mason et al. is a substantial improvement over the hinges of De Camp and Rolfes, it is noted that the hinge of Mason et al. utilizes the same rotation limiting assembly for two different functions. In particular, the rotation limiting assembly is used to set a desired hinge rotation limit as well as to selectively lock the hinge against rotation altogether. Therefore, it is necessary to remove the rotation limiting assembly from its selected rotation limiting position and place the rotation limiting assembly in the locked position when it is desired to lock the hinge against rotation. When it is desired to enable rotation by unlocking the hinge, the rotation limiting assembly is removed from the locked position and returned to its selected rotation limiting position. This sequence of steps inherently increases the risk of erroneously resetting the hinge rotation limit when the rotation limiting assembly is returned to the rotation limiting position if the user has forgotten or improperly locates the prior prescribed hinge rotation limit. Therefore, a need exists for a hinge for an orthopedic brace having an adjustable rotation range, further wherein the hinge is selective between a locked mode and an unlocked mode of operation without disrupting the selected hinge rotation limits.

Accordingly, it is an generally an object of the present invention to provide a hinge for an orthopedic brace, which has an adjustable rotation range, and which has a locked and an unlocked mode of operation. More particularly, it is an object of the present invention to provide such a hinge having a rotation limiting mechanism, which selectively enables adjustment of the hinge rotation range, and also having a locking mechanism, which selectively enables locking the hinge against rotation altogether. It is still another object of the present invention to provide such a hinge, wherein the locking mechanism can be transitioned between the locked and unlocked modes without altering the rotation limits of the rotation limiting mechanism.

In some instances, it is desirable to enable the user or provider of the orthopedic brace to adjust the dimensions of the rigid components. This feature allows the manufacture of a single adjustable orthopedic brace which is capable of being fitted to a number of different sized users. This feature also allows the manufacture of an orthopedic brace which is capable of being adapted over time to the evolving therapeutic treatment requirements of a single user. For example, a user often requires an orthopedic brace providing a high degree of immobility and/or stability immediately following surgery to a skeletal joint such as the knee. Generally, an orthopedic brace, which extends virtually the entire length of the limb on either side of the afflicted skeletal joint, i.e., the upper and lower leg in the case of the knee, provides the highest degree of immobility and/or stability. Therefore, post-operative knee braces typically have relatively long rigid support members for mounting on the leg above and below the knee.

As rehabilitation of the repaired skeletal joint progresses following surgery, an orthopedic brace providing an increased degree of mobility is usually desirable while possibly tolerating a lesser degree of stability. The mobility of an orthopedic brace can often be increased simply by shortening the length of the rigid support members. Thus, an orthopedic brace with rigid support members having an adjustable length are highly desirable for post-operative application. The adjustable orthopedic brace obviates the need and expense of periodically replacing the initial orthopedic brace with gradually less restrictive orthopedic braces as rehabilitation progresses.

Therefore, it is another object of the present invention to provide an orthopedic brace with rigid supports which have adjustable dimensions. In particular, it is an object of the present invention to provide an orthopedic brace with rigid longitudinal supports which have adjustable lengths. It is further an object of the present invention to provide such an adjustable orthopedic brace, wherein adjustment of the rigid supports to alternate dimensions is relatively simple. It is another object of the present invention to provide such an adjustable orthopedic brace, wherein the rigid supports reliably maintain their alternate adjusted dimensions during normal use of the brace until it is desired to readjust the dimensions. These objects and others are accomplished in accordance with the invention described hereafter.

SUMMARY OF THE INVENTION

One characterization of the present invention is an adjustable support assembly for an orthopedic brace comprising a support arm, a housing and a locking mechanism. The housing includes a travel track which slidably receives the support arm. The locking mechanism includes a lock lever selectively transitionable between a closed position and an open position. When the lock lever is in the closed position, the lock lever applies a sufficient degree of a pressing force to the support arm to prevent slidable displacement of the support arm in the travel track. The lock lever preferably applies the pressing force to the support arm in a force direction essentially perpendicular to a travel direction of the support arm in the travel track. When the lock lever is in the open position, the lock lever withdraws a sufficient degree of the pressing force from the support arm to enable slidable displacement of the support arm in the travel track.

The lock lever preferably has a head rotationally mounted on the housing and the locking mechanism further includes a lock chamber formed in the housing to receive the head. The lock chamber has an internal opening which enables access to the support arm in the travel track from the lock chamber. In accordance with a specific embodiment of the present characterization, the head engages the support arm through the internal opening to apply the pressing force to the support arm when the lock lever is in the closed position. In accordance with an alternate specific embodiment of the present characterization, the locking mechanism includes a friction plate positioned in the internal opening. The friction plate engages the head and the support arm when the lock lever is in the closed position and the lock lever applies the pressing force to the support arm via the friction plate. The friction plate preferably has a first layer engageable with the head and a second layer engageable with the support arm. The first layer is formed from a relatively non-compressible material and the second layer is formed from a relatively elastically compressible material.

Another characterization of the present invention is an orthopedic brace comprising a first support assembly having a first support arm, a first housing and a first locking mechanism. The first housing includes a first travel track which slidably receives the first support arm. The first locking mechanism includes a first lock lever selectively transitionable between a first closed position and a first open position. When the first lock lever is in the first closed position, the first lock lever applies a sufficient degree of a first pressing force to the first support arm to prevent slidable displacement of the first support arm in the first travel track. When the first lock lever is in the first open position, the first lock lever withdraws a sufficient degree of the first pressing force from the first support arm to enable slidable displacement of the first support arm in the first travel track.

The orthopedic brace further comprises a second support assembly having a second support arm, a second housing and a second locking mechanism. The second housing includes a second travel track which slidably receives the second support arm. The second locking mechanism includes a second lock lever selectively transitionable between a second closed position and a second open position. When the second lock lever is in the second closed position, the second lock lever applies a sufficient degree of a second pressing force to the second support arm to prevent slidable displacement of the second support arm in the second travel track. When the second lock lever is in the second open position, the second lock lever withdraws a sufficient degree of the second pressing force from the second support arm to enable slidable displacement of the second support arm in the second travel track.

The orthopedic brace still further comprises a joint connecting the first support assembly to the second support assembly. The joint is preferably either a static joint or a rotational hinge.

Another characterization of the present invention is an adjustable support assembly for an orthopedic brace comprising a support arm, a housing and a travel limit. The support arm has an edge with an indentation formed therein to define a step on the edge at a terminus of the indentation. The housing includes a travel track slidably receiving the support arm. The travel limit is positioned in the travel track and is preferably a post mounted in the housing. The indentation clears the travel limit when the support arm is slidably displaced in a travel direction within the travel track, but the travel limit engages the step when the support arm is slidably displaced in the travel direction within the travel track to a position where the step is aligned with the travel limit. As such, the travel limit prevents further slidable displacement of the support arm in the travel direction within the travel track.

In accordance with a specific alternate embodiment of the present characterization, the adjustable support assembly further comprises a locking mechanism including a lock lever selectively transitionable between a closed position and an open position. When the lock lever is in the closed position, the lock lever applies a sufficient degree of a pressing force to the indentation to prevent slidable displacement of the support arm in the travel track. When the lock lever is in the open position, the lock lever withdraws a sufficient degree of the pressing force from the indentation to enable slidable displacement of the support arm in the travel track.

Another characterization of the present invention is a method for adjusting the length of a support assembly for an orthopedic brace. The method provides a support assembly having a support arm and a housing with a travel track. The travel track is sized to receive the support arm therein and the support assembly has a plurality of selected lengths, each selected length corresponding to a different position of the support arm in the travel track. The support arm is positioned in the travel track at a first position such that the support assembly has a first selected length. The support arm is then slidably displaced in a travel direction in the travel track to a second position such that the support assembly has a second selected length different than the first selected length. The support arm is locked in the second position to maintain the support assembly at the second selected length by applying a pressing force in a force direction to the support arm sufficient to prevent slidable displacement of the support arm in the travel track.

Another characterization of the present invention is a hinge for an orthopedic brace comprising a first rotation plate, a second rotation plate, a pivotal connector connecting the first and second rotation plates, a rotation limiting mechanism, and a rotation locking mechanism. The first rotation plate has a first peripheral edge, an inner face, and an outer face. The second rotation plate has a second peripheral edge.

The rotation limiting mechanism includes a rotation limiting face formed in the second peripheral edge and a rotation limiting assembly selectively positionable in a fixed position relative to the first rotation plate. The rotation limiting assembly has a stop face engageable with the rotation limiting face upon rotation of the second rotation plate relative to the first rotation plate in a first rotation direction, which substantially limits further rotation of the second rotation plate relative to the first rotation plate in the first rotation direction.

The rotation locking mechanism includes a rotation lock pin and a series of lock notches formed in the second peripheral edge. The rotation lock pin is selectively positionable within one of the series of lock notches, which substantially locks the first and second rotation plates against rotation of the second rotation plate relative to the first rotation plate in the first rotation direction or in a second rotation direction opposite the first rotation direction.

In accordance with specific embodiments, the rotation limiting mechanism includes a series of rotation limiting teeth formed in the inner face at the first peripheral edge. The rotation limiting assembly has an engagement face which is selectively positionable between two adjacent teeth of the series of teeth to place the rotation limiting assembly in the fixed position. The rotation limiting mechanism further includes a biasing member biasing the engagement face radially inward from the first peripheral edge.

The rotation locking mechanism includes a lock pin slot formed in the inner face and a lock actuator assembly engaging the rotation lock pin. The rotation lock pin is slidably positioned in the lock pin slot. The rotation lock pin has a longitudinal axis and the lock actuator assembly maintains the longitudinal axis of the rotation lock pin substantially perpendicular to the inner face. Alternatively or additionally, the lock pin slot has a longitudinal axis and the lock actuator assembly maintains the longitudinal axis of the rotation lock pin substantially perpendicular to the longitudinal axis of the lock pin slot.

The rotation lock pin is transitionable between a locked position and an unlocked position. The rotation lock pin is transitioned to the locked position by selectively positioning the rotation lock pin within one of the series of lock notches as recited above. The rotation lock pin is transitioned to the unlocked position by selectively withdrawing the rotation lock pin from one of the series of lock notches so that the rotation lock pin does not substantially impede rotation of the second rotation plate relative to the first rotation plate in the first or second rotation direction. The rotation lock pin can be transitionable between the locked and unlocked positions without substantially modifying the fixed position of the rotation limiting assembly.

The rotation locking mechanism further includes a lock transition plate and a lock actuator assembly engaging the rotation lock pin. The lock transition plate has a lock assembly cut-out and the lock actuator assembly has an actuator bar selectively and slidably positioned in the lock assembly cut-out. The lock assembly cut-out has a bordering edge with a first depression and a second depression formed therein and the actuator bar has a protrusion configured for close fitting within the first or second depression when the actuator bar is selectively slid within the lock assembly cut-out.

In accordance with an alternate embodiment, the present invention is a hinge for an orthopedic brace comprising a first external rotation plate, an internal rotation plate, a second external rotation plate, a pivotal connector connecting the first and second external rotation plates and internal rotation plate, a rotation limiting mechanism, and a rotation locking mechanism. The first external rotation plate has a first external peripheral edge, a first external inner face and a first external outer face. The internal rotation plate has an internal peripheral edge. The second external rotation plate has a second external peripheral edge, a second external inner face and a second external outer face.

The rotation limiting mechanism includes a series of rotation limiting teeth formed in the first external inner face at the first external peripheral edge, a rotation limiting face formed in the internal peripheral edge, and a rotation limiting assembly. The rotation limiting assembly has an engagement face selectively positionable between two adjacent teeth of the series of teeth to place the rotation limiting assembly in a fixed position. The rotation limiting assembly also has a stop face engageable with the rotation limiting face upon rotation of the internal rotation plate relative to the first external rotation plate in a first rotation direction which substantially limits further rotation of the internal rotation plate relative to the first external rotation plate in the first rotation direction.

The rotation locking mechanism includes a series of lock notches formed in the internal peripheral edge, a rotation lock pin, and a lock pin slot. The lock pin slot is formed in the first and second external inner faces, is formed only in the first external inner face, or is formed only in the second internal face. The rotation lock pin is slidably positioned in the lock pin slot and is selectively positionable within one of the series of lock notches, which substantially locks the first external rotation plate and the internal rotation plate against rotation of the internal rotation plate relative to the first external rotation plate in the first rotation direction or in a second rotation direction opposite the first rotation direction.

In accordance with a specific embodiment, the engagement face is a first engagement face and the rotation limiting mechanism further includes a series of rotation limiting teeth formed in the second external inner face at the second external peripheral edge. The rotation limiting assembly has a second engagement face selectively positionable between two adjacent teeth of the series of teeth in the second external inner face.

In accordance with another alternate embodiment, the present invention is a rotation locking mechanism for a hinge of an orthopedic brace. The hinge has a first rotation plate with a first peripheral edge, an inner face and an outer face, a second rotation plate with a second peripheral edge, and a pivotal connector connecting the first and second rotation plates. The rotation locking mechanism comprises a rotation lock pin, a series of lock notches formed in the second peripheral edge, and a lock pin slot formed in the inner face. The rotation lock pin is slidably positioned in the lock pin slot and is selectively positionable within one of the series of lock notches, which substantially locks the first and second rotation plates against rotation of the second rotation plate relative to the first rotation plate in a first rotation direction or in a second rotation direction opposite the first rotation direction.

The rotation locking mechanism further comprises a lock actuator assembly engaging the rotation lock pin. The rotation lock pin has a longitudinal axis and the lock actuator assembly maintains the longitudinal axis of the rotation lock pin substantially perpendicular to the inner face. The rotation locking mechanism further comprises a lock transition plate having a lock assembly cut-out. The lock actuator assembly has an actuator bar which is selectively and slidably positioned in the lock assembly cut-out. The lock assembly cut-out has a bordering edge with a first depression and a second depression formed therein and the actuator bar has a protrusion configured for close fitting within the first or second depression when the actuator bar is selectively slid within the lock assembly cut-out.

The rotation lock pin is transitionable between a locked position and an unlocked position. The rotation lock pin is transitioned to the locked position by selectively positioning the rotation lock pin within one of the series of lock notches as recited above. The rotation lock pin is transitioned to the unlocked position by selectively withdrawing the rotation lock pin from one of the series of lock notches so that the rotation lock pin does not substantially impede rotation of the second rotation plate relative to the first rotation plate in the first or second rotation direction.

The present invention will be further understood from the drawings and the following detailed description.

BRIEF DESCRIPTION OF THE DRAWINGS

FIG. 6 is a detailed cross-sectional view of the locking mechanism in the support assembly of FIG. 4, which is taken along line 6-6 (shown in FIG. 5), wherein the locking mechanism is in the closed position.

FIG. 7 is a detailed cross-sectional view of the locking mechanism in the support assembly of FIG. 4, wherein the locking mechanism is in an open position.

FIGS. 14A and 14B are an exploded perspective view of the hinge of FIG. 13.

DESCRIPTION OF PREFERRED EMBODIMENTS

Figure 1:
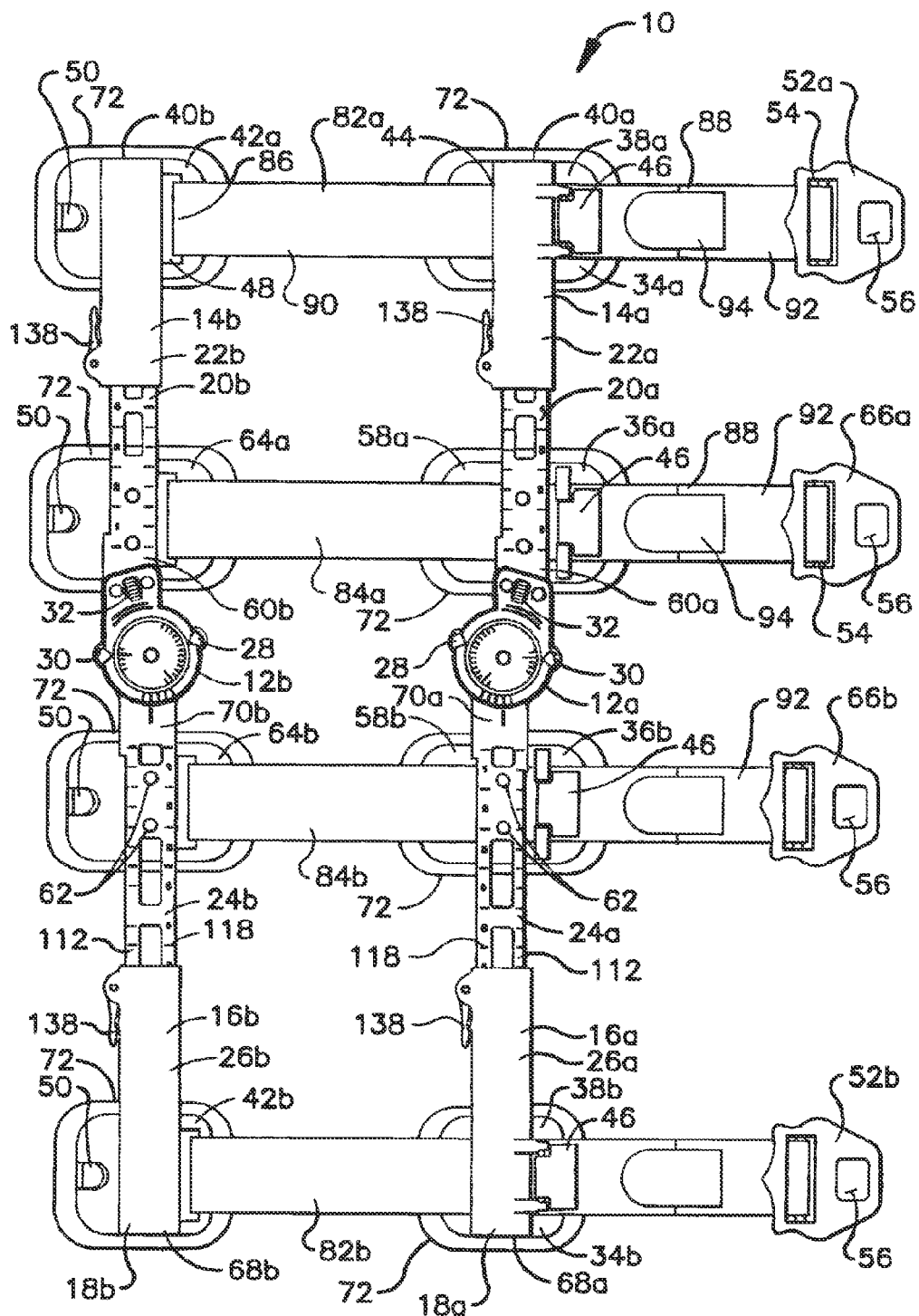
FIG. 1 is a plan view of an orthopedic brace including a plurality of support assemblies having the length-adjusting and locking mechanisms of the present invention.

Referring initially to FIG. 1, an orthopedic brace is shown and generally designated 10. There are a number of relative terms defined below which are used in the following description to distinguish various elements of the orthopedic brace 10 from one another, but which are not to be construed as limiting the scope of the invention. The relative terms "medial" and "lateral" characterize certain elements of the orthopedic brace 10 and, in particular, describe the relative proximity of the given element to the central longitudinal axis of the body of the user when the brace 10 is mounted thereon. A "medial" element is closer to the central longitudinal axis of the body, while a "lateral" element is further from the central longitudinal axis of the body.

The terms "proximal" and "distal" characterize certain elements of the brace 10, which are aligned with the longitudinal axis of the brace 10. The terms describe the relative proximity of the given element to the central joint of the brace 10. A "proximal" element is closer to the central joint of the brace 10, while a "distal" element is further from the central joint of the brace 10. The terms "upper" and "lower" likewise characterize certain elements of the brace 10, which are aligned with the longitudinal axis of the brace 10. However, the terms describe the position of the given element as being either above or below a horizontal plane running through the central joint of the brace 10. In particular, an "upper" element is above the horizontal plane running through the central joint of the brace 10, while a "lower" element is below the horizontal plane running through the central joint of the brace 10.

The relative terms "posterior" and "anterior" characterize certain elements of the orthopedic brace 10 and, in particular, describe the orientation of the given element relative to the central longitudinal axis of the body of the user when the brace 10 is mounted thereon. A "posterior" element is positioned behind the central longitudinal axis of the body in correspondence with the posterior of the body, while an "anterior" element is positioned in front of the central longitudinal axis of the body in correspondence with the posterior of the body.

The orthopedic brace 10 comprises a lateral central joint 12a, a lateral upper support assembly 14a and a lateral lower support assembly 16a, which in combination define a lateral longitudinal brace assembly 18a. The lateral upper support assembly 14a includes a lateral upper support arm 20a and a lateral upper housing 22a. The lateral lower support assembly 16a similarly includes a lateral lower support arm 24a and a lateral lower housing 26a, having a construction substantially similar to the lateral upper support arm 20a and lateral upper housing 22a, respectively. The lateral central joint 12a connects the lateral upper support assembly 14a with the lower support assembly 16a such that the lateral upper and lower support assemblies 14a, 16a extend radially from the lateral central joint 12a. Details of the lateral upper and lower support assemblies 14a, 16a are described below in association with the length-adjusting and locking mechanisms of the present invention.

The lateral central joint 12a is preferably a dynamic joint, which dynamically connects the lateral upper and lower support assemblies 14a, 16a, and is more preferably a rotational hinge, which rotationally connects the lateral upper and lower support assemblies 14a, 16a. The lateral central joint 12a is most preferably a releasably locking rotational hinge with adjustable rotation limits as shown herein. The releasably locking rotational hinge includes a flexion rotation stop 28, an extension rotation stop 30 and a lock actuator 32. Further details of the structure and operation of the releasably locking rotational hinge are described in detail below and are likewise disclosed in commonly-owned U.S. Pat. No. 7,235,059 issued on Jun. 26, 2007 entitled "Releasably Locking Hinge for an Orthopedic Brace Having Adjustable Rotation Limits".

Notwithstanding the above, it is understood that the lateral central joint 12a is not limited to any one specific construction or type of joint. Thus, most conventional hinges for orthopedic braces, which enable rotation of the lateral upper longitudinal support assembly 14a and/or the lateral lower longitudinal support assembly 16a about the hinge, are alternatively employed as the lateral central joint 12a of the orthopedic brace 10. Exemplary prior art hinges are disclosed in U.S. Pat. Nos. 401,933; 4,481,941; 5,672,152; and 5,827,208. In yet another alternative, not shown, the lateral central joint 12a is a static joint which does not enable rotation of the lateral upper longitudinal support assembly 14a and/or the lateral lower longitudinal support assembly 16a about the joint. In accordance with this embodiment, the positions of the lateral upper support assembly 14a, lateral lower support assembly 16a, and lateral central joint 12a are all fixed relative to one another and the resulting orthopedic brace 10 functions solely as a splint.

The orthopedic brace 10 further comprises a medial central joint 12b, a medial upper support assembly 14b and a medial lower support assembly 16b, which in combination define a medial longitudinal brace assembly 18b. The construction of the medial longitudinal brace assembly 18b is essentially the same as the lateral longitudinal brace assembly 18a. As such, the medial upper support assembly 14b includes a medial upper support arm 20b and a medial upper housing 22b and the medial lower support assembly 16b similarly includes a medial lower support arm 24b and a medial lower housing 26b. The medial central joint 12b connects the medial upper support assembly 14b with the medial lower support assembly 16b such that the medial upper and lower support assemblies 14b, 16b extend radially from the medial central joint 12b.

The orthopedic brace 10 additionally comprises an upper distal strap retention assembly 34a and an upper proximal strap retention assembly 36a, both of which are associated with the lateral and medial upper support assemblies 14a, 14b. The upper distal strap retention assembly 34a includes an upper distal strap guide member 38a integral with a distal end 40a of the lateral upper housing 22a and an upper distal strap connection member 42a integral with a distal end 40b of the medial upper housing 22b. The upper distal strap guide member 38a has a strap guide loop 44 and a rotationally-connected strap lock 46 positioned adjacent to the strap guide loop 44. The upper distal strap connection member 42a has a strap anchor loop 48 and a strap connection hook 50 positioned on opposite sides of the upper distal strap connection member 42a.

The upper distal strap guide and connection members 38a, 42a are preferably fabricated from a relatively rigid material, such as a high-strength plastic, and have an arcuate configuration, which corresponds to the contours of the body of a user on whom the orthopedic brace 10 is to be mounted in a manner described below. The upper distal strap retention assembly 34a further includes an upper distal strap attachment member 52a likewise preferably fabricated from a relatively rigid high-strength plastic. The upper distal strap attachment member 52a has a strap attachment loop 54 and a strap connection loop 56 positioned on opposite sides of the upper distal strap attachment member 52a.

The upper proximal strap retention assembly 36a includes an upper proximal strap guide member 58a attached to a proximal end 60a of the lateral upper support arm 20a by fasteners 62, such as rivets, and an upper proximal strap connection member 64a attached to a proximal end 60b of the medial upper support arm 20b likewise by fasteners 62. The upper proximal strap retention assembly 36a further includes an upper proximal strap attachment member 66a. The upper proximal strap guide member 58a, upper proximal strap connection member 64a, and upper proximal strap attachment member 66a have essentially the same construction as the upper distal strap guide member 38a, upper distal strap connection member 42a, and upper distal strap attachment member 52a, respectively. Accordingly, components common to corresponding members are designated by the same reference characters.

The orthopedic brace 10 still further comprises a lower distal strap retention assembly 34b and a lower proximal strap retention assembly 36b, each of which is associated with both the lateral and medial lower support assemblies 16a, 16b. The lower distal strap retention assembly 34b is essentially the same as the upper distal strap retention assembly 34a. As such, the lower distal strap retention assembly 34b includes a lower distal strap guide member 38b integral with a distal end 68a of the lateral lower housing 26a, a lower distal strap connection member 42b integral with a distal end 68b of the medial lower housing 26b, and a lower distal strap attachment member 52b.

The lower proximal strap retention assembly 36b is essentially the same as the upper proximal strap retention assembly 36a. As such, the lower proximal strap retention assembly 36b includes a lower proximal strap guide member 58b attached to a proximal end 70a of the lateral lower support arm 24a by fasteners 62, a lower proximal strap connection member 64b attached to a proximal end 70b of the medial lower support arm 24b by fasteners 62, and a lower proximal strap attachment member 66b. The lower distal and lower proximal strap guide members 38b, 58b, lower distal and lower proximal strap connection members 42b, 64b, and lower distal and lower proximal strap attachment members 52b, 66b have essentially the same construction as the upper distal and upper proximal strap guide members 38a, 58a, upper distal and upper proximal strap connection members 42a, 64a, and upper distal and upper proximal strap attachment members 52a, 66a, respectively. Accordingly, components common to corresponding members are designated by the same reference characters.

A pad 72 is preferably provided in association with each upper and lower distal strap guide and connection member 38a, 38b, 42a, 42b and each upper and lower proximal strap guide and connection member 58a, 58b, 64a, 64b. The pads 72 are affixed to the inner face of each of the members 38a, 38b, 42a, 42b, 58a, 58b, 64a, 64b by fastening means (not shown), such as hook and loop fasteners commonly termed VELCRO. The pads 72 cushion the body of the user from the relatively hard, rigid surfaces of the orthopedic brace 10 when the orthopedic brace 10 is mounted on the body.

Figure 2:
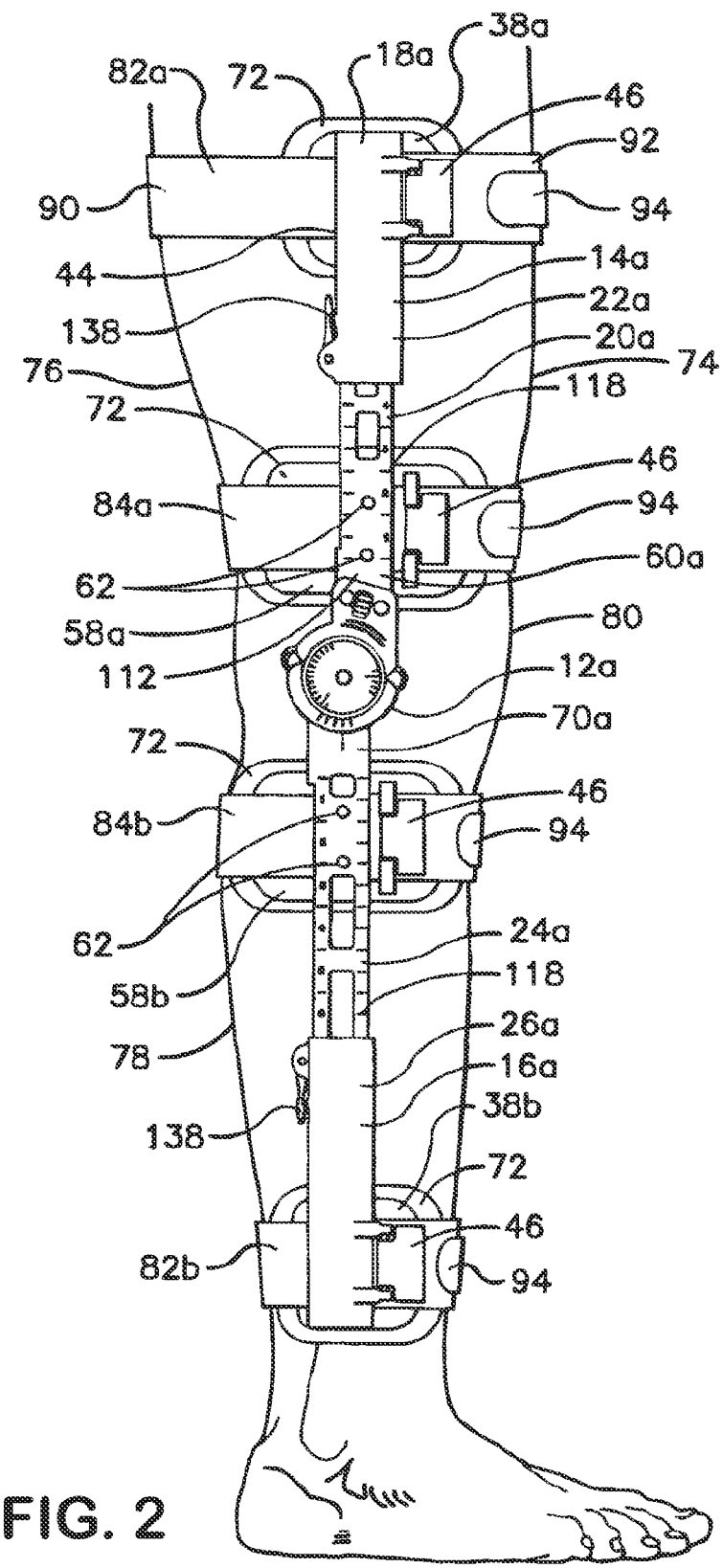
FIG. 2 is a lateral view of the orthopedic brace of FIG. 1 mounted on the leg of a user.
Figure 3:
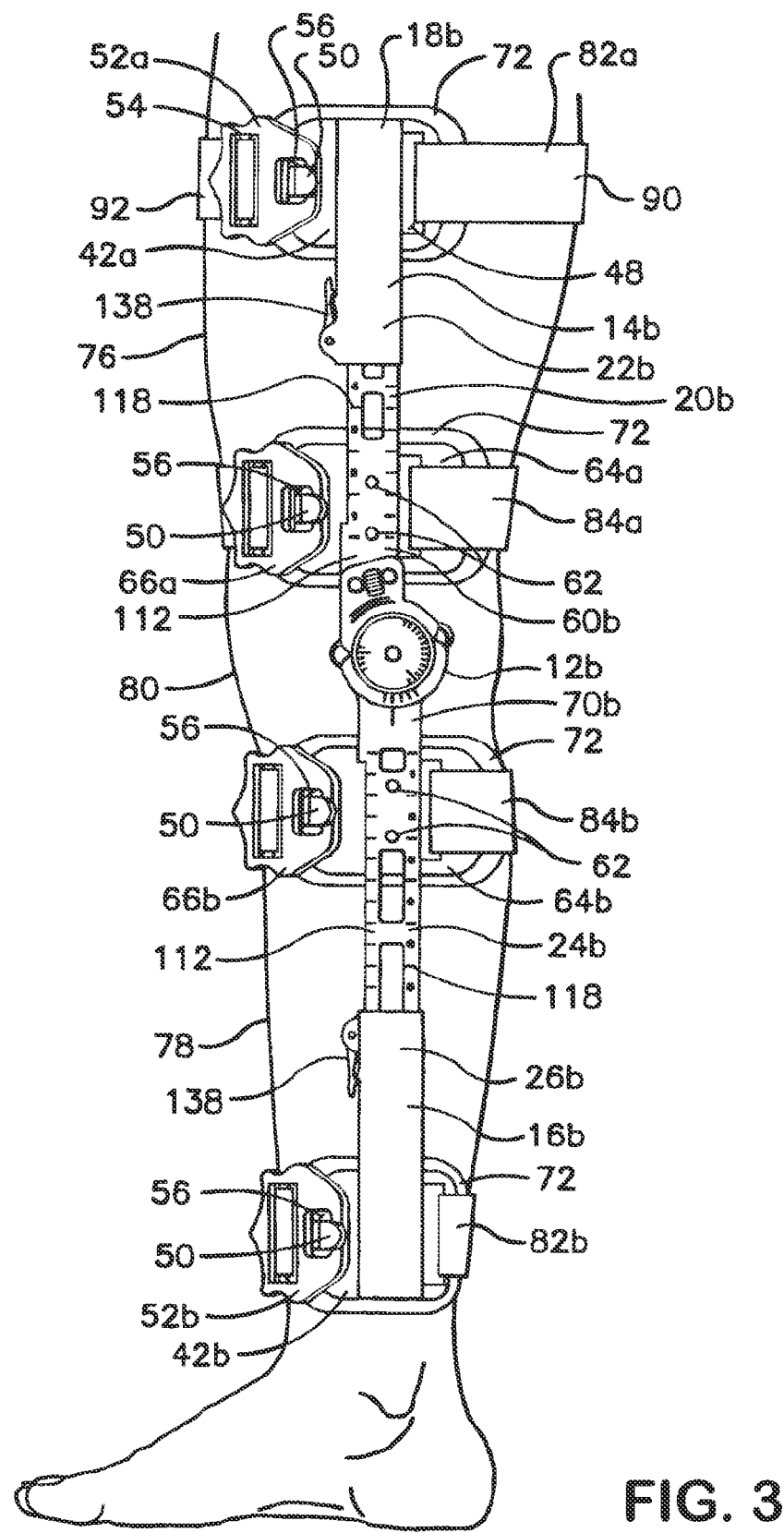
FIG. 3 is a medial view of the orthopedic brace of FIG. 1 mounted on the leg of a user.
Figure 4:
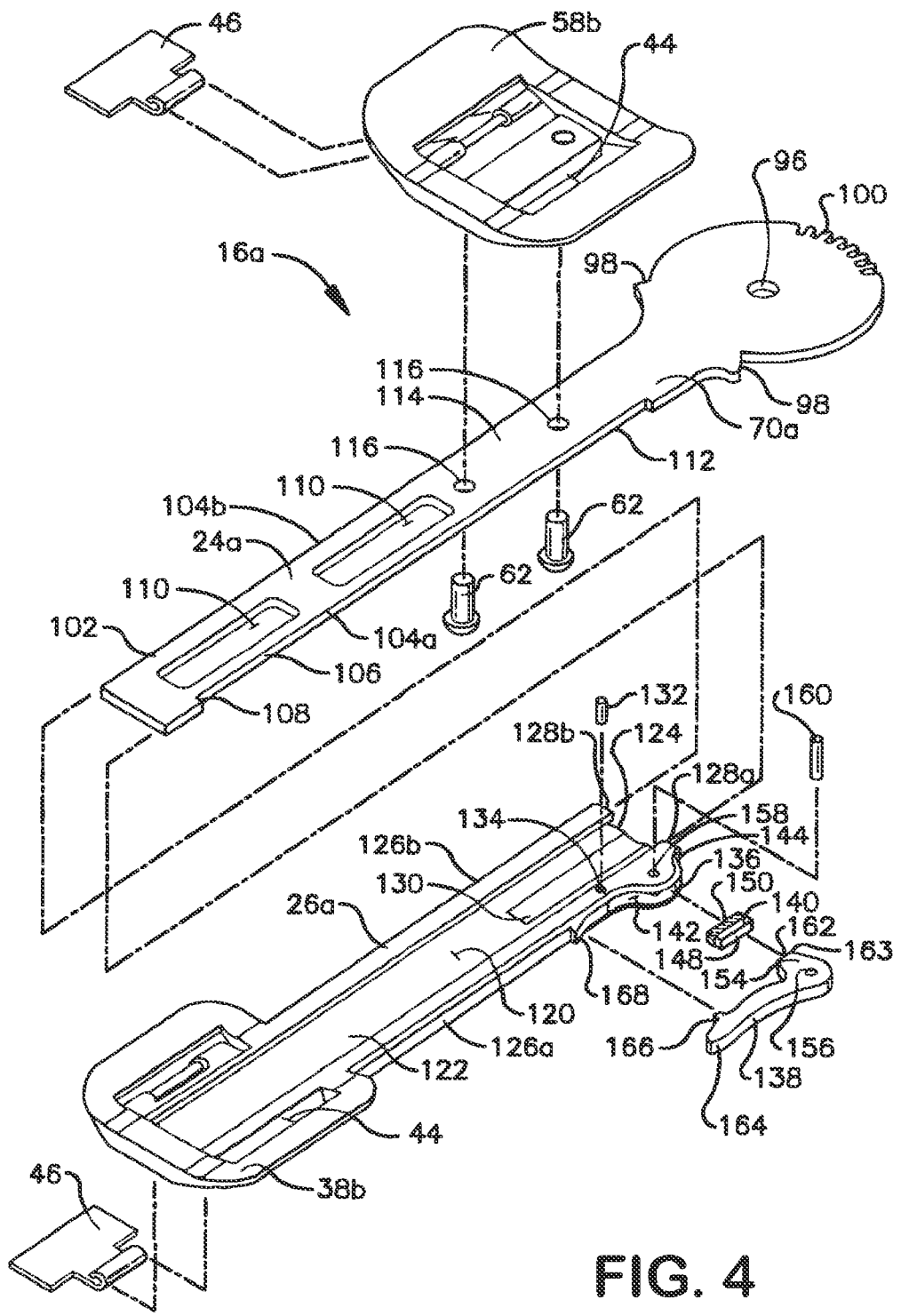
FIG. 4 is an exploded rear perspective view of a support assembly of the orthopedic brace of FIG. 1.

For purposes of illustration, the orthopedic brace 10 shown and described herein is a specific type of orthopedic brace commonly termed a post-operative knee brace. Full utility of the orthopedic brace 10 is achieved when the orthopedic brace 10 is mounted on the leg of a user. Referring additionally to FIGS. 2 and 3, the orthopedic brace 10 is mounted on the right leg 74, which is characterized as having an upper leg 76, a lower leg 78, and a knee joint 80 rotationally connecting the upper and lower legs 76, 78. It will be apparent to the skilled artisan that the post-operative knee brace 10 is likewise adaptable for mounting on the left leg (not shown) of the user.

The orthopedic brace 10 is further provided with a plurality of straps which engage the strap retention assemblies to retain the orthopedic brace 10 on the leg 74 during use. In particular, an upper distal strap 82a engages the upper distal strap retention assembly 34a and an upper proximal strap 84a engages the upper proximal strap retention assembly 36a. A lower distal strap 82b similarly engages the lower distal strap retention assembly 34b and a lower proximal strap 84b engages the lower proximal strap retention assembly 36b.

Engagement of the upper distal strap 82a with the upper distal strap retention assembly 34a is effected by anchoring a first end 86 of the upper distal strap 82a to the strap anchor loop 48 of the upper distal strap connection member 42a by relatively permanent fastening means, such as sewing. The second end 88 of the upper distal strap 82a is threaded through the strap guide loop 44 of the upper distal strap guide member 38a to define a posterior segment 90 of the upper distal strap 82a extending between the upper distal strap connection member 42a and upper distal strap guide member 38a. The length of the posterior segment 90 is adjusted in correspondence with the size of the leg 74 and releasably fixed by fastening the strap lock 46 on the upper distal strap guide member 38a to the upper distal strap 82a using fastening means (not shown), such as hook and loop fasteners mounted on the inner face of the strap lock 46 and outer face of the upper distal strap 82a. As such, the posterior segment 90 of the upper distal strap 82a posteriorly connects the lateral and medial longitudinal brace assemblies 18a, 18b.

The second end 88 of the upper distal strap 82a extending from the upper distal strap guide member 38a is threaded through the strap attachment loop 54 of the upper distal strap attachment member 52a to define an anterior segment 92 of the upper distal strap 82a extending between the upper distal strap guide member 38a and upper distal strap attachment member 52a. The length of the anterior segment 92 is adjusted in correspondence with the size of the leg 74 and releasably fixed by doubling the second end 88 back over the upper distal strap 82a. A fastening tab 94 attached to the second end 88 provides fastening means, such as hook and loop fasteners, for fastening the second end 88 onto the upper distal strap 82a. With the orthopedic brace 10 mounted on the leg 74, the anterior segment 92 of the upper distal strap 82a and the upper distal strap attachment member 52a are drawn away from the upper distal strap guide member 38a across the anterior of the upper leg 76 to the upper distal strap connection member 42a, where the strap connection loop 56 of the upper distal strap attachment member 52a loops over the strap connection hook 50 of the upper distal strap connection member 42a. As such, the anterior segment 92 of the upper distal strap 82a anteriorly connects the lateral and medial longitudinal brace assemblies 18a, 18b. Thus, the posterior and anterior segments 90, 92 of the upper distal strap 82a in combination completely encircle the leg 74.

Engagement of the lower distal strap 82b with the lower distal strap retention assembly 34b, the upper proximal strap 84a with the upper proximal strap retention assembly 36a, and the lower proximal strap 84b with the lower proximal strap retention assembly 36b is effected in a substantially similar manner as described above with respect to the upper distal strap 82a and upper distal strap retention assembly 34a. As such, the upper distal strap 82a, lower distal strap 82b, upper proximal strap 84a, and lower proximal strap 84b closely secure the orthopedic brace 10 to the leg 74 of the user.

When the orthopedic brace 10 is properly mounted on and closely secured to the leg 74, the lateral central joint 12a is positioned adjacent to the lateral side of the knee joint 80 and the medial central joint 12b is positioned adjacent to the medial side of the knee joint 80. The lateral upper longitudinal support assembly 14a is positioned adjacent to the lateral side of the upper leg 76 is longitudinally aligned with the lateral side of the upper leg 76. The medial upper longitudinal support assembly 14b is positioned adjacent to the medial side of the upper leg 76 and is longitudinally aligned with the medial side of the upper leg 276. The lateral lower longitudinal support assembly 16a is similarly positioned adjacent to the lateral side of the lower leg 78 and is longitudinally aligned with the lateral side of the lower leg 78. The medial lower longitudinal support assembly 16b is positioned adjacent to the medial side of the lower leg 78 and is longitudinally aligned with the medial side of the lower leg 78.

Referring to FIGS. 4-7, the lateral lower support assembly 16a and associated strap guide members 38b, 58b are shown and described hereafter in greater detail. As recited above, the lateral lower support assembly 16a includes a lateral lower support arm 24a and a lateral lower housing 26a. Both are preferably fabricated from lightweight, high-strength, relatively rigid materials. The lateral lower support arm 24a is more preferably fabricated from a metal, such as aluminum or stainless steel, and the lateral lower housing 26a is more preferably fabricated from a molded plastic. The proximal end 70a of the lateral lower support arm 24a is configured to cooperatively engage the lateral central joint 12a. For example, if the lateral central joint 12a is a releasably locking rotational hinge as shown herein, the proximal end 70a is preferably configured with a hinge pivot aperture 96 to enable rotation of the lateral lower support arm 24a about the lateral central joint 12a and with a plurality of rotation limiting faces 98 and rotation lock notches 100 to enable the rotation limiting and rotation locking functions of the hinge, respectively. Notwithstanding the above, it is understood that the proximal end 70a of the lateral lower support arm 24a is not limited to any one specific configuration, but can have any number of alternate configurations, which cooperatively correspond with the particular function, construction and configuration of the lateral central joint 12a.

The remainder of the lateral lower support arm 24a, extending from the proximal end 70a to a distal end 102, has an elongate bar-like configuration with first and second longitudinal edges 104a, 104b on opposite sides of the lateral lower support arm 24a. The first longitudinal edge 104a is essentially linear, but has a shallow indentation 106 extending along the majority of its length. The indentation 106 extends from immediately adjacent to the tip of the distal end 102 toward the proximal end 70a of the lateral lower support arm 24a. The distal terminus of the indentation 106 defines a step which provides the lateral lower support arm 24a with a travel stop 108. The second longitudinal edge 104b is likewise linear, but in contrast to the first longitudinal edge 104a is smooth and continuous along its entire length.

A plurality of cut-outs 110 are formed through entire thickness of the lateral lower support arm 24a, thereby extending from the outer face 112 to the inner face 114 of the lateral lower support arm 24a. The cut-outs 110 reduce the weight of the lateral lower support arm 24a and correspondingly reduce the overall weight of the orthopedic brace 10 without significantly diminishing the structural strength and integrity of the lateral lower support arm 24a. Fastening apertures 116 are also formed through the entire thickness of the lateral lower support arm 24a, which enable attachment of the lower proximal strap guide member 58b to the lateral lower support arm 24a by means of the fasteners 62. The outer face 112 of the lateral lower support arm 24a is provided with a plurality of graduated length markers 118 (shown in FIGS. 1-3), which enable the user to determine the selected length of the lateral lower support assembly 16a as described below.

The lateral lower housing 26a includes a length-adjusting mechanism for guiding sliding displacement of the lateral lower support arm 24a relative to the lateral lower housing 26a and a locking mechanism for selectively preventing sliding displacement of the lateral lower support arm 24a. The length-adjusting mechanism comprises a travel track 120 formed in and partially enclosed by the lateral lower housing 26a. The front of the travel track 120 is bounded by an inner face 122 of the lateral lower housing 26a. The distal end of the travel track 120 is bounded by the distal end 68a of the lateral lower housing 26a, while the proximal end of the travel track corresponds to a proximal end 124 of the lateral lower housing 26a, which is open and unbounded.

The sides of the travel track 120 are bounded by first and second rails 126a, 126b, which extend from the inner face 122 in an essentially perpendicular direction. A first lip 128a extends perpendicularly from the first rail 126a and a second lip 128b likewise extends perpendicularly from the second rail 126b. The first and second lips 128a, 128b each project over a portion of the inner face 122 of the lateral lower housing 26a on opposite sides thereof to partially bound the back of the travel track 120 while the remainder of the back of the travel track 120 is open. Thus, the first rail 126a and first lip 128a in combination and the second rail 126b and second lip 128b in combination each has the configuration of an inverted "L".

The lateral lower support arm 24a is telescopingly fitted within the travel track 120 for slidable displacement therein. In particular, the lateral lower support arm 24a is positioned in the travel track 120 of the lateral lower housing 26a such that the outer face 112 of the lateral lower support arm 24a is adjacent to the inner face 122 of the lateral lower housing 26a, the first and second longitudinal edges 104a, 104b are adjacent to the first and second rails 126a, 126b, respectively, and the inner face 114 is adjacent to the first and second lips 128a, 128b. The width of the inner face 122 is at least slightly greater than the width of the lateral lower support arm 24a at its widest point within the travel track 120 (typically at the travel stop 108) and the height of the first and second rails 126a, 126b (i.e., the distance from the inner face 122 to the inside of the first and second lips 128a, 128b) is at least slightly greater than the thickness of the lateral lower support arm 24a. A clearance slot 130 is formed in the inner face 122 of the lateral lower housing 26a, which enables the heads of the fasteners 62 on the lateral lower support arm 24a to clear the inner face 122 of the lateral lower housing 26a.

Slidable displacement of the lateral lower support arm 24a within the travel track 120 is distally constrained by the closed distal end 68a of the lateral lower housing 26a in cooperation with the distal end 102 of the lateral lower support arm 24a and is proximally constrained by the travel stop 108 of the lateral lower support arm 24a in cooperation with a travel limit post 132 positioned in the travel track 120. The travel limit post 132 extends into the travel track 120 via a post aperture 134 formed through the first lip 128a. The travel limit post 132 and travel stop 108 prevent the user from inadvertently withdrawing the lateral lower support arm 24a in its entirety from the travel track 120 via the open proximal end 124 of the lateral lower housing 26a when slidably displacing the lateral lower support arm 24a in the proximal direction within the travel track 120. The closed distal end 68a of the lateral lower housing 26a stops the distal end 102 of the lateral lower support arm 24a when slidably displacing the lateral lower support arm 24a in the distal direction within the travel track 120.

The locking mechanism comprises a lock chamber 136 and a lock lever 138. FIGS. 4-10 show a specific embodiment of the locking mechanism which further comprises an optional friction plate 140. The lock chamber 136 is formed in the first rail 126a of the lateral lower housing 26a. The lock chamber 136 is open to the exterior of the lateral lower housing 26a via an external opening 142 which is bounded on opposite sides by sidewalls 144. The lock chamber 136 is also open to the travel track 120 via an internal opening 146.

The friction plate 140 has a laminate construction. A first layer 148 of the friction plate 140 is preferably formed from a rigid non-compressible material, such as a metal. A second layer 150 of the friction plate 140 is preferably formed from a material having a relatively high coefficient of static friction in association with the material of the lateral lower support arm 24a, such as an elastically compressible material and more particularly an elastomer.

The friction plate 140 is sized in correspondence with the lock chamber 136 and internal opening 146 to enable fitted positioning of the friction plate 140 within the lock chamber 136 and internal opening 146. In particular, the length and width of the friction plate 140 are at least slightly smaller than the length and width of the internal opening 146 so that the friction plate 140 fits within the internal opening 146 when the friction plate 140 is positioned in the lock chamber 136. The friction plate 140 is preferably oriented in the lock chamber 136 such that the first layer 148 faces the lock lever 138 while the second layer 150 extends through the internal opening 146 and faces the lateral lower support arm 24a housed in the travel track 120. As such, the internal opening 146 enables the second layer 150 to engage the lateral lower support arm 24a and, more particularly, enables the friction plate 140 to selectively press against the indentation 106 in the first longitudinal edge 104a of the lateral lower support arm 24a when a sufficient pressing force is applied to the friction plate 140 in the direction of the travel track 120 as described hereafter.

The lock lever 138 includes a head 154 having an oblong configuration. A lever pivot aperture 156 is formed through the head 154 and lever pivot apertures 158 are formed through the sidewalls 144 of the lock chamber 136. The lever pivot apertures 156, 158 are all aligned with one another and a lever pivot pin 160 is fitted through the apertures 156, 158 and retained therein to enable manual rotation of the head 154 within the lock chamber 136 about the lever pivot pin 160. Accordingly, the head 154 is rotationally displaceable relative to the friction plate 140 and lateral lower support arm 24a.

Figure 5:
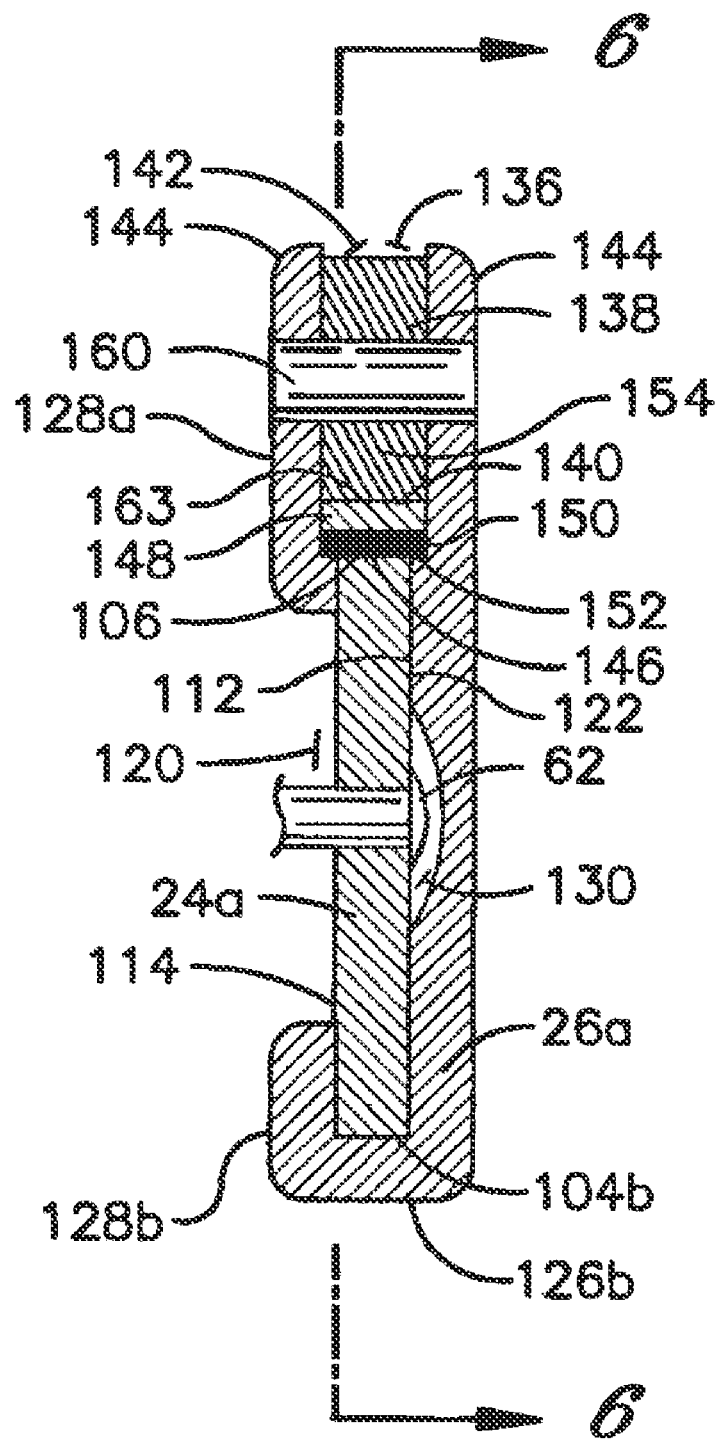
FIG. 5 is detailed cross-sectional view of the locking mechanism in the support assembly of FIG. 4, which is taken along line 5-5 (shown in FIG. 6), wherein the locking mechanism is in a closed position.

The oblong-shaped head 154 has an elongated end 162 termed a force applicator which has a relatively straight flat surface bounded on one side by a leading edge 163. When the head 154 is rotationally positioned such that the force applicator 162 is adjacent the first layer 148 of the friction plate 140, the elongated force applicator 162 engages the first layer 148 and applies a pressing force to the friction plate 140 and the underlying lateral lower support arm 24a. This cooperative arrangement of the components of the locking mechanism is termed the locked or closed position and is shown in FIGS. 5 and 6. The configuration of the head 154, the pressing force of the head 154 against the friction plate 140, and the friction forces between the head 154 and friction plate 140 enable the head 154 to resist rotational displacement in the clockwise direction (when viewed from the front rather than from the rear as in FIGS. 4 and 6) and enable the locking mechanism to maintain the closed position in the absence of any overriding external rotational forces applied to the lock lever 138 in the clockwise direction.

The components of the locking mechanism are selectively repositionable from the closed position to a second cooperative arrangement termed the open or unlocked position shown in FIG. 7 by applying a sufficient overriding external rotational force to the lock lever 138 to overcome the resistance of the head 154 to rotational displacement. In particular, an overriding external rotational force is applied to the lock lever 138 in the clockwise direction which is sufficient to rotate the head 154 in a clockwise direction from the closed position until the leading edge 163 clears the friction plate 140. The locking mechanism achieves the open position when the force applicator 162 disengages from the first layer 148 of the friction plate 140, thereby reducing the pressing force of the head 154 on the friction plate 140, and preferably fully withdrawing the pressing force from the friction plate 140. The locking mechanism is selectively returned to the closed position by applying an external rotational force to the lock lever 138 in a counter-clockwise direction until the leading edge 163 passes the friction plate 140 and the force applicator 162 is again adjacent the first layer 148, thereby engaging the first layer 148 and applying a pressing force to the friction plate 140 and the underlying lateral lower support arm 24a.

The lock lever 138 also has a lever arm 164 attached to the head 154. The lever arm 164 extends through the external opening 142 out of the lock chamber 136. A first lock catch 166 is integrally formed on the side of the lever arm 164 facing the lateral lower housing 26a. A cooperative second lock catch 168 is likewise integrally formed on the lateral lower housing 26a in correspondence with the first lock catch 166. When the locking mechanism is in the closed position, the first and second lock catches 166, 168 are in press-fitting engagement with one another to additionally resist rotational displacement of the head 154 in the clockwise direction and to provide a visual indicator that the locking mechanism is in the closed position. When the overriding external rotational force is applied to the lock lever 138 sufficient to rotate the head 154 in the clockwise direction, the first and second lock catches 166, 168 are simultaneously released from press-fitting engagement with one another.

The construction of the lateral and medial upper support assemblies 14a, 14b and medial lower support assembly 16b is essentially the same as the construction of the lateral lower support assembly 16a. Accordingly, the above-recited description of the lateral lower support assembly 16a applies equally to the remaining support assemblies 14a, 14b, 16b.

Figure 8:
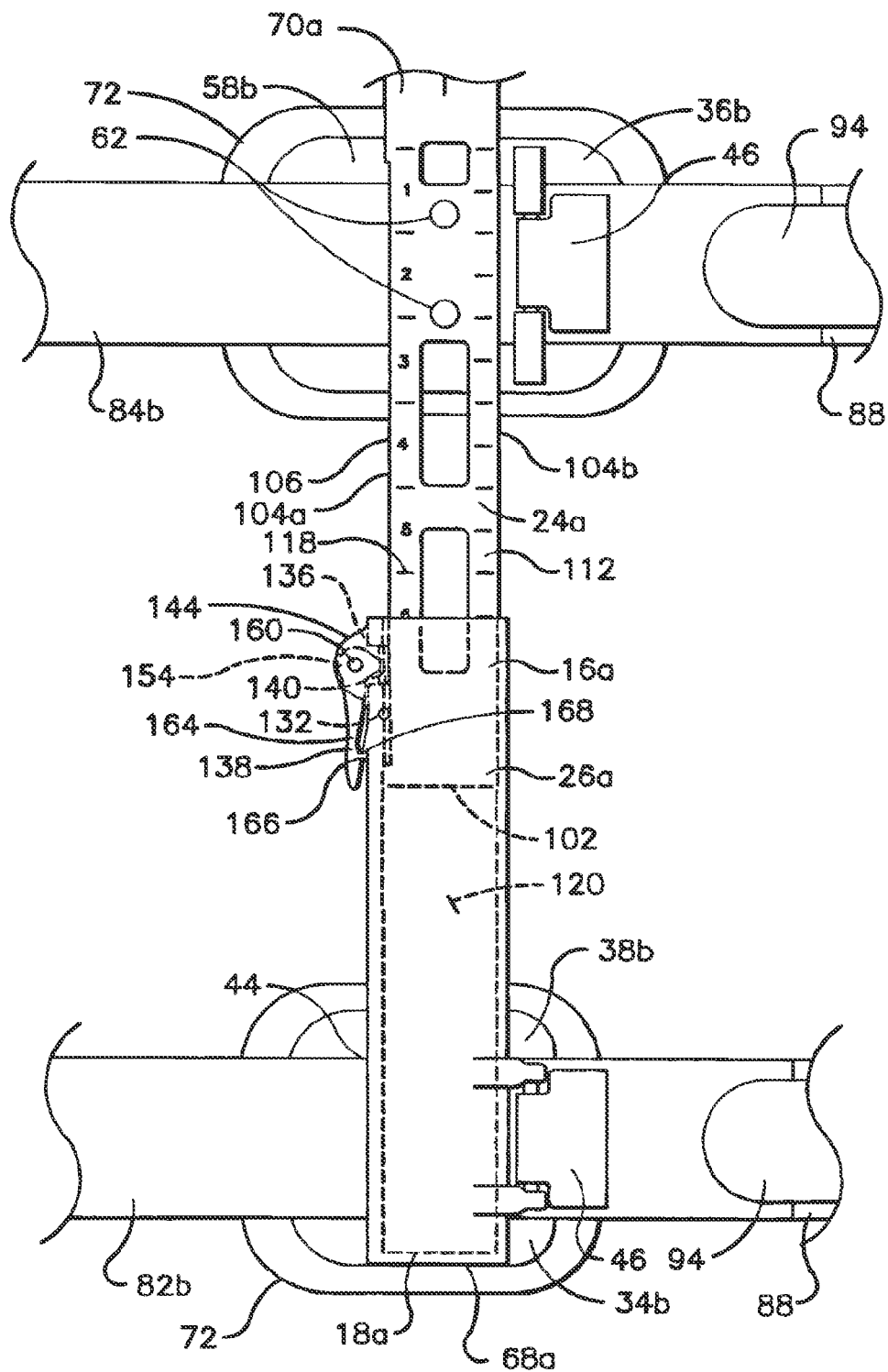
FIG. 8 is a front elevational view of the support assembly of FIG. 4 in a locked mode of operation, wherein the support assembly is fixed at a first selected length.

Exemplary operation of a support assembly of the orthopedic brace 10 is shown and described below in greater detail with reference to the lateral lower support assembly 16a and FIGS. 8-10. Referring initially to FIG. 8, the lateral lower support assembly 16a is in a locked mode of operation. Accordingly, the locking mechanism of the lateral lower support assembly 16a is in a closed position, which fixes the length of the lateral lower support assembly 16a. In the present case, the length of the lateral lower support assembly 16a is fixed at a first selected length, which is an extended length similar to that shown in FIG. 1 at or near the upper length limit of the lateral lower support assembly 16a.

In accordance with the closed position, the first lock catch 166 on the lever arm 164 and the second lock catch 168 on the lateral lower housing 26a are press fitted together and the force applicator 162 on the head 154 of the lock lever 138 engages the first layer 148 of the friction plate 140, thereby applying a pressing force to the friction plate 140 in the direction of the travel track 120. The pressing force causes the second layer 150 of the friction plate 140 to press against the indentation 106 in the first longitudinal edge 104a of the lateral lower support arm 24a with a substantial force. This force, coupled with the relatively high coefficient of static friction for the materials of the second layer 150 and lateral lower support arm 24a, essentially prevents slidable displacement of the lateral lower support arm 24a in either direction within the travel track 120 when subjected to normally encountered operational forces, thereby maintaining the length of the lateral lower support assembly 16a fixed at the first selected length.

Figure 9:
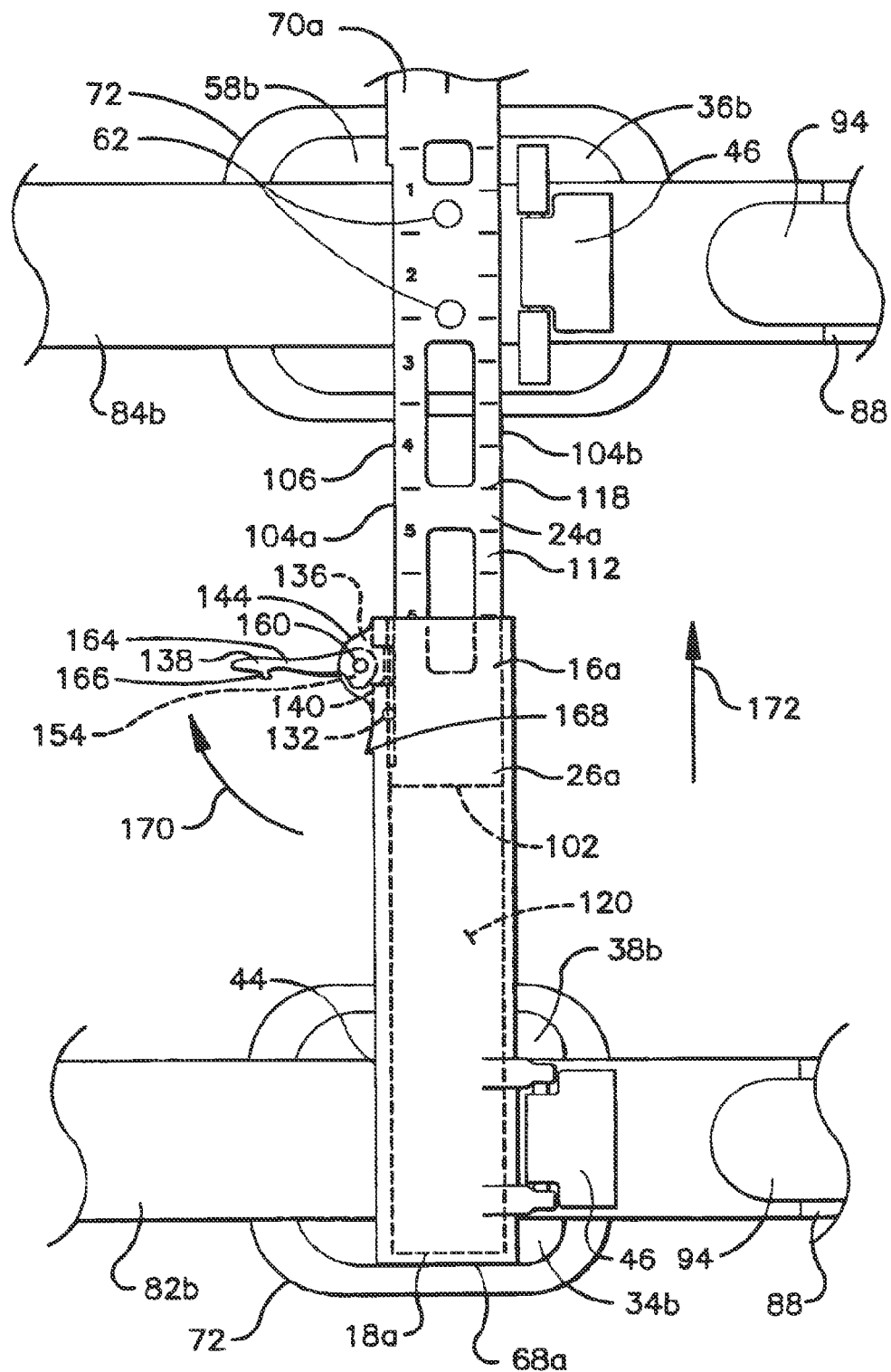
FIG. 9 is a front elevational view of the support assembly of FIG. 4 in an adjustment mode of operation, wherein the support assembly is adjustable to an alternate selected length.

Referring to FIG. 9, the lateral lower support assembly 16a is in an adjustment mode of operation. The locking mechanism has been transitioned to an open position, which correspondingly enables operation of the length-adjusting mechanism of the lateral lower support assembly 16a. The locking mechanism is transitioned to the open position by manually applying an overriding external rotational force to the lever arm 164 in a clockwise direction which is sufficient to overcome the resistance of the head 154 to rotational displacement. Rotational displacement of the lever arm 164 and head 154 in the clockwise direction releases the first lock catch 166 from the second lock catch 168 and correspondingly disengages the force applicator 162 from the first layer 148 of the friction plate 140, which causes the pressing force to be withdrawn from the friction plate 140 and underlying lateral lower support arm 24a. Accordingly, there is no longer a sufficient force to prevent linear displacement of the lateral lower support arm 24a within the travel track 120 when subjected to relatively low linear displacement forces.

The length-adjusting mechanism permits a user to select an alternate length of the lateral lower support assembly 16a different than the first selected length when the locking mechanism is in the open position. For example, it may be desirable to adjust the length of the lateral lower support assembly 16a from the extended first selected length to a second selected length, which is a shortened length, i.e., shorter than extended length. The length of the lateral lower support assembly 16a is adjusted to the second selected length preferably by removing the orthopedic brace from the leg, if this has not already been done prior to the locking mechanism transitioning step. A sufficient upward linear displacement force is manually applied to the lateral lower housing 26a, which in the present case is in the direction of arrow 172, to slidably displace the lateral lower support arm 24a within the travel track 120 and telescope the lateral lower support arm 24a into the lateral lower housing 26a.

Figure 10:
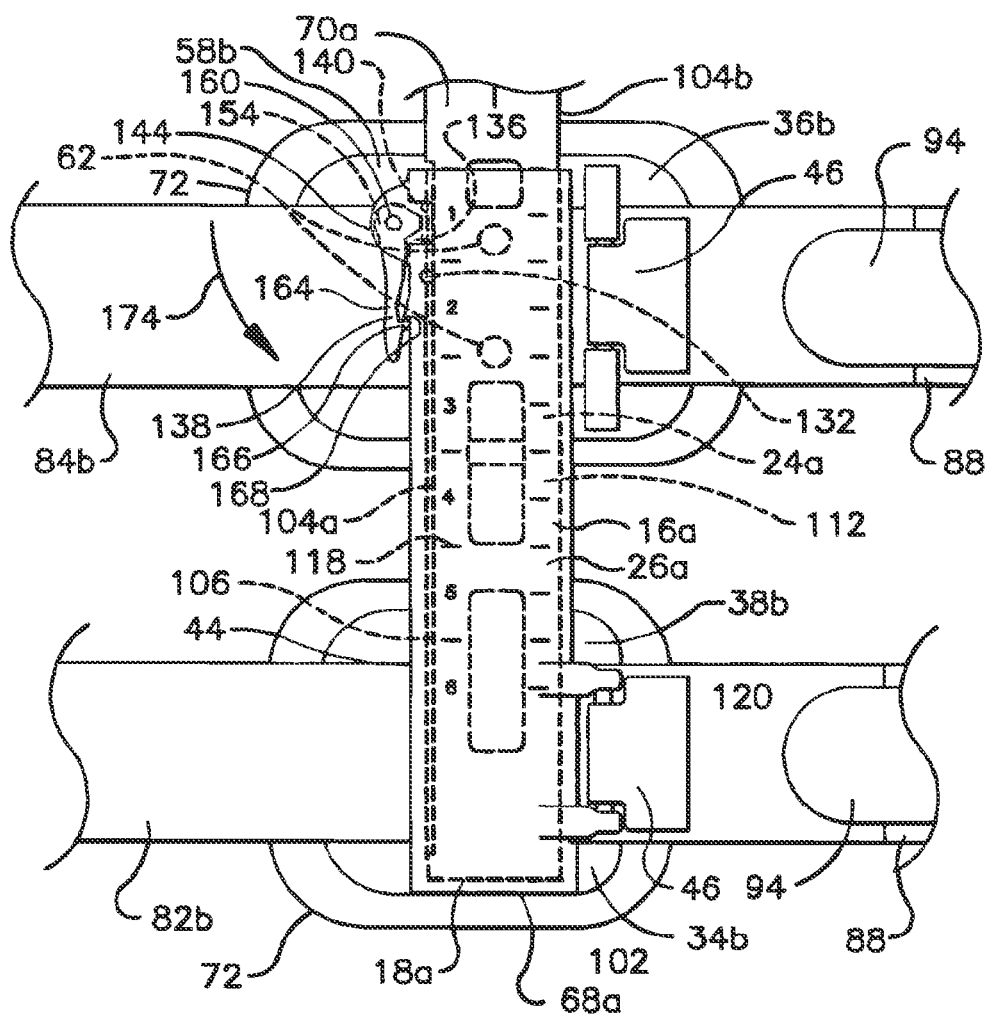
FIG. 10 is a front elevational view of the support assembly of FIG. 4 in the locked mode of operation, wherein the support assembly has been adjusted to a second selected length.

Referring to FIG. 10, the lateral lower support assembly 16a is transitioned back to the locked mode of operation after completing the length adjusting step so that the orthopedic brace may be remounted on the leg. The locking mechanism of the lateral lower support assembly 16a is shown again in the closed position, which essentially prevents linear displacement of the lateral lower support arm 24a in either direction within the travel track 120. In the present case, the length of the lateral lower support assembly 16a is fixed at the second selected length, which was selected in the length adjusting step near the lower length limit of the lateral lower support assembly 16a where the lower distal strap guide member 38a approaches the lower proximal strap guide member 58a.

The locking mechanism is retransitioned to the closed position by reversing the locking mechanism transitioning step described above. In particular, the lever arm 164 and correspondingly the head 154 are manually rotated in the counter-clockwise direction of arrow 174 until the leading edge 163 of the force applicator 162 passes the friction plate 140 and the force applicator 162 is adjacent to and engaging the first layer 148 of the friction plate 140. The first and second lock catches 166, 168 are also press fitted together. The resulting position of the lever arm 164 and head 154 applies a sufficient pressing force to the friction plate 140 and underlying lateral lower support arm 24a to prevent linear displacement of the lateral lower support arm 24a in either direction within the travel track 120, thereby maintaining the length of the lateral lower support assembly 16a fixed at the second selected length.

Operation of the lateral and medial upper support assemblies 14a, 14b and medial lower support assembly 16b is essentially the same as operation of the lateral lower support assembly 16a. Accordingly, the above-recited description of operation of the lateral lower support assembly 16a applies equally to the remaining support assemblies 14a, 14b, 16b. In general, it is desirable to fix a selected length of both the lateral and medial upper support assemblies 14a, 14b which is essentially equal and to correspondingly fix a selected length of both the lateral and medial lower support assemblies 16a, 16b which is essentially equal. However, the selected length of the upper support assemblies 14a, 14b need not be fixed equal to the selected length of the lower support assemblies 16a, 16b. Indeed, in many instances, the selected length of the upper support assemblies 14a, 14b is substantially shorter than the fixed length of the lower support assemblies 16a, 16b.

Figure 11:
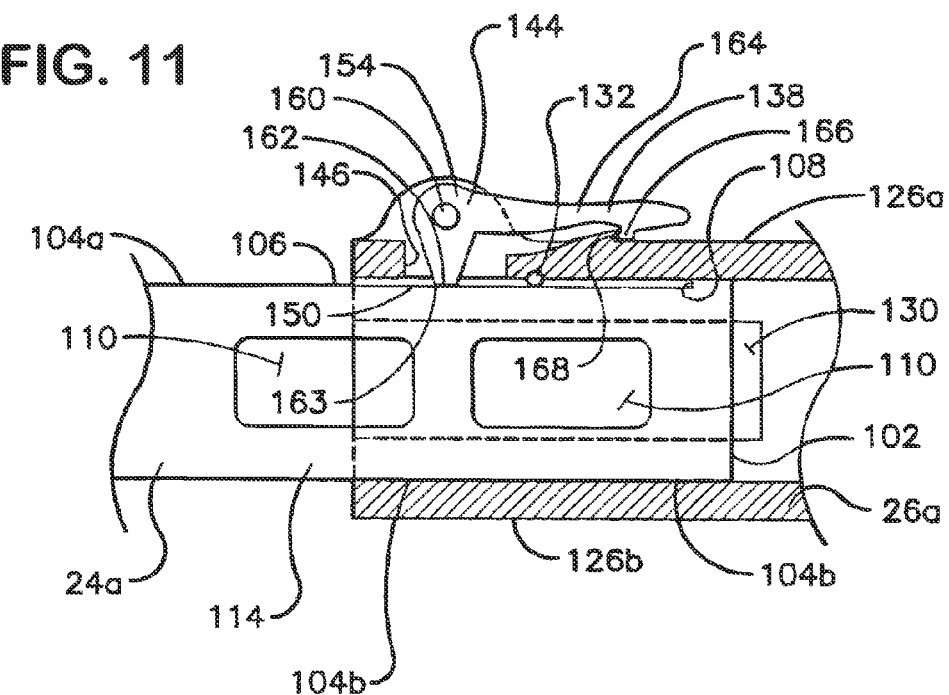
FIG. 11 is a detailed cross-sectional view of an alternate embodiment of a locking mechanism having utility in the support assemblies of the orthopedic brace of FIG. 1, wherein the locking mechanism is in the closed position.
Figure 12:
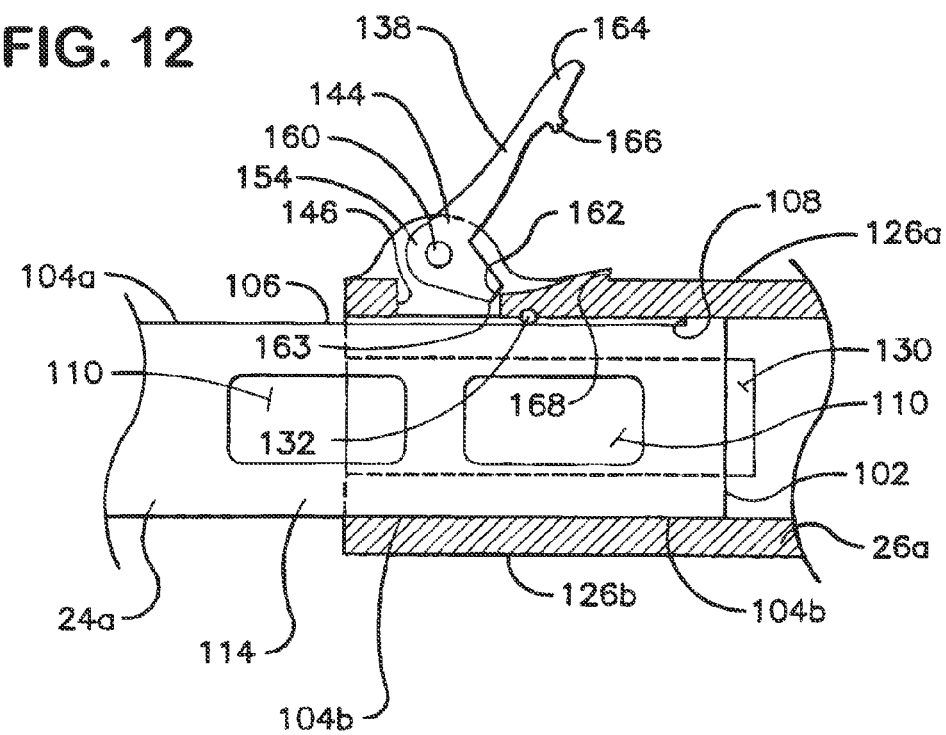
FIG. 12 is a detailed cross-sectional view of the locking mechanism of FIG. 11, wherein the locking mechanism is in the open position.

An alternate embodiment of the locking mechanism having utility in the support assemblies of the orthopedic brace shown in FIGS. 1-3 is described hereafter with reference to FIGS. 11 and 12. The locking mechanism of the present alternate embodiment is substantially the same as the previous embodiment shown in FIGS. 4-10 except that the present locking mechanism omits the friction plate. Accordingly, the elements of FIGS. 11 and 12, which are common to FIGS. 4-10, are denoted by the same reference characters.

The present locking mechanism comprises a lock chamber 136 and a lock lever 138. The lock chamber 136 is formed in the lateral lower housing 26a and has an internal opening 146. The lock lever 138 includes an oblong-shaped head 154 and a lever arm 164 which are rotationally displaceable relative to the lateral lower support arm 24a. The head 154 is sized in correspondence with the lock chamber 136 and internal opening 146 to enable fitted positioning of the head 154 within the lock chamber 136 and internal opening 146. In particular, the head 154 has a force applicator 162 with a length and width at least slightly smaller than the length and width of the internal opening 146 so that the force applicator 162 fits within the internal opening 146 when the head 154 is positioned in the lock chamber 136. The head 154 is preferably oriented in the lock chamber 136 such that the force applicator 162 extends through the internal opening and faces the lateral lower support arm 24a housed in the travel track 120. As such, the internal opening 146 enables the force applicator 162 to engage the lateral lower support arm 24a and, more particularly, enables the force applicator 162 to selectively press directly against the indentation 106 in the first longitudinal edge 104a of the lateral lower support arm 24a in the direction of the travel track 120.

When the head 154 is rotationally positioned such that the force applicator 162 is adjacent the lateral lower support arm 24a, the force applicator 162 engages the lateral lower support arm 24a and applies a pressing force thereto. This cooperative arrangement of the components of the locking mechanism is termed the locked or closed position and is shown in FIG. 11. The configuration of the head 154, the pressing force of the head 154 against the lateral lower support arm 24a, and the friction forces between the head 154 and lateral lower support arm 24a enable the head 154 to resist rotational displacement in the clockwise direction (when viewed from the front rather than from the rear as in FIG. 11) and enable the locking mechanism to maintain the closed position in the absence of any overriding external rotational forces applied to the lock lever 138 in the clockwise direction.

The components of the locking mechanism are selectively repositionable from the closed position to a second cooperative arrangement termed the open or unlocked position shown in FIG. 12 by applying a sufficient overriding external rotational force to the lock lever 138 to overcome the resistance of the head 154 to rotational displacement. In particular, an overriding external rotational force is applied to the lock lever 138 in a clockwise direction which is sufficient to rotate the head 154 in a clockwise direction from the closed position until the leading edge 163 of the force applicator 162 clears the lateral lower support arm 24a. The locking mechanism achieves the open position when the force applicator 162 disengages from the lateral lower support arm 24a, thereby reducing the pressing force of the head 154 on the lateral lower support arm 24a, and preferably fully withdrawing the pressing force from the lateral lower support arm 24a. The locking mechanism is selectively returned to the closed position by applying an external rotational force to the lock lever 138 in a counter-clockwise direction until the leading edge 163 passes the lateral lower support arm 24a and the force applicator 162 is again adjacent the lateral lower support arm 24a, thereby engaging the lateral lower support arm 24a and applying a pressing force thereto.

Although the brace components of the present invention have been described above for purposes of illustration as applying to a post-operative knee brace, it is apparent from the foregoing that the above-recited brace components are readily adaptable to other types of orthopedic braces for the knee or other joints of the body in addition to post-operative knee braces. It is additionally noted that each set of upper support arm, central joint, and lower support arm in the embodiment of the post-operative knee brace described above is a series discrete interconnected components. However, in accordance with an alternate embodiment of the present invention not shown, either the upper support arm or the lower support arm can be integrally formed with the central joint as a continuous structure, which cooperatively functions with the remaining non-integrated support arm. In accordance with another alternate embodiment of the present invention not shown, the position of any housing and correspondingly paired support arm can be reversed so that the upper housing and/or lower housing is more proximal to the central joint than the correspondingly paired upper and/or lower support arm. As such the housing is attached to or integral with the central joint rather than the correspondingly paired support arm, although the support arm remains slidably displaceable within the housing. In accordance with yet another alternate embodiment of the present invention not shown, the upper support arm, central joint, and lower support arm (or alternatively upper housing, central joint, and lower housing) can be integrally formed together as a single continuous static structure, wherein the resulting orthopedic brace functions as a splint having an adjustable length.

Figure 13:
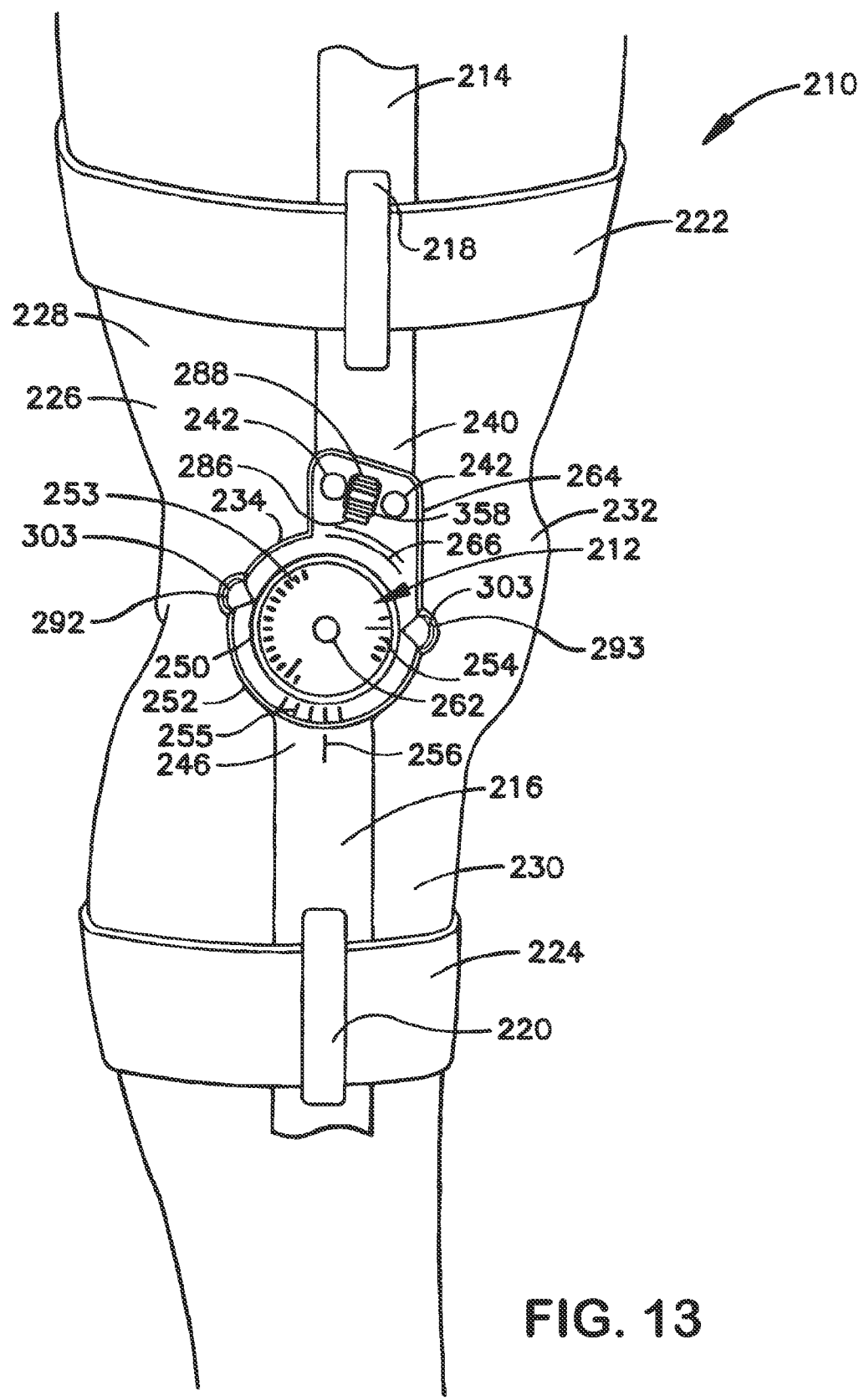
FIG. 13 is a side view of a leg having an orthopedic brace employing the hinge of the present invention mounted thereon.

Referring to FIG. 13, an alternate hinged orthopedic brace of the present invention is shown and generally designated 210. There are a number of relative terms defined below which are used in the following description to distinguish various elements of the brace 210 from one another, but which are not to be construed as limiting the scope of the invention.

The relative terms "medial" and "lateral" characterize certain elements of the brace 210, which are positioned about the axis of rotation of the brace 210. The terms describe the relative proximity of the given element to the central longitudinal axis of the body of the user when the brace 210 is mounted thereon. In particular, a "medial" element is closer to the central longitudinal axis of the body, while a "lateral" element is further from the central longitudinal axis of the body.

The relative terms "inner" and "outer" likewise characterize certain elements of the brace 210, which are positioned about the axis of rotation of the brace 210. However, the terms describe the relative proximity of the given element to the central longitudinal axis of the brace 210. An "inner" element is closer to the central longitudinal axis of the brace 210, while an "outer" element is further from the central longitudinal axis of the brace 210.

The terms "proximal" and "distal" characterize certain elements of the brace 210, which are aligned with the longitudinal axis of the brace 210. The terms describe the relative proximity of the given element to the axis of rotation of the brace 210. A "proximal" element is closer to the axis of rotation of the brace 210, while a "distal" element is further from the axis of rotation of the brace 210.

The terms "upper" and "lower" likewise characterize certain elements of the brace 210, which are aligned with the longitudinal axis of the brace 210. However, the terms describe the position of the given element as being either above or below a horizontal plane bisected by the axis of rotation of the brace 210. In particular, an "upper" element is above the horizontal plane bisecting the axis of rotation of the brace 210, while a "lower" element is below the horizontal plane bisecting the axis of rotation of the brace 210.

The hinged orthopedic brace 210 comprises a hinge 212, an upper rotation arm 214, a lower rotation arm 216, an upper strap retainer 218 associated with the upper rotation arm 214, and a lower strap retainer 220 associated with the lower rotation arm 216. The upper strap retainer 218 maintains an upper strap 222 distally connected to the upper rotation arm 214, while the lower strap retainer 220 maintains a lower strap 224 distally connected to the lower rotation arm 216.

For purposes of illustration, the hinged orthopedic brace 210 is a specific type of hinged orthopedic brace commonly termed a post-operative knee brace. The brace 210 is mounted on a right leg 226 of a user, which is characterized as having an upper leg 228, a lower leg 230 and a knee joint 232 rotationally connecting the upper and lower legs 228, 230. It is apparent to the skilled artisan that the post-operative knee brace 210 is alternatively adaptable for mounting on the left leg of a user. It is further apparent from the foregoing that the above-recited brace components 212, 214, 216, 218, 220, 222, 224 are readily adaptable to other types of hinged orthopedic braces for the knee and other joints of the body.

Both the upper and lower rotation arms 214, 216 are preferably relatively rigid, being formed from a lightweight, high-strength material, such as aluminum or stainless steel. When the brace 210 is mounted on the leg 226, the upper rotation arm 214 is longitudinally aligned with the lateral side of the upper leg 228, the hinge 212 is aligned with the lateral side of the knee joint 232 and the lower rotation arm 216 is longitudinally aligned with the lateral side of the lower leg 230. In particular, the longitudinal axis of the upper rotation arm 216 is oriented substantially parallel to the longitudinal axis of the upper leg 228 and is retained in removable engagement with the upper leg 228 by means of the upper strap 222 and upper strap retainer 218. The longitudinal axis of the lower rotation arm 216 is oriented substantially parallel to the longitudinal axis of the lower leg 230 and is retained in removable engagement with the lower leg 230 by means of the lower strap 224 and lower strap retainer 220.

Although not shown, it is within the scope of the present invention to provide relatively rigid, fitted, upper and lower leg cuffs attached to or integral with the upper and lower rotation arms 214, 216 which further secure the upper and lower rotation arms 214, 216 to the upper and lower legs 228, 230, respectively. It is also within the scope of the present invention to provide additional straps and strap retainers which further secure the upper and lower rotation arms 214, 216 to the upper and lower legs 228, 230, respectively. It is further within the scope of the present invention to reverse the configuration of the brace 210 in a manner readily apparent to the skilled artisan so that the upper rotation arm 214 is repositioned in longitudinal alignment with the lateral side of the lower leg 230 and the lower rotation arm 216 is repositioned in longitudinal alignment with the lateral side of the upper leg 228, while the hinge 212 remains aligned with the lateral side of the knee joint 232. In another alternative, the upper rotation arm 214 can be longitudinally aligned with the medial side of the upper leg 228, the hinge 212 aligned with the medial side of the knee joint 232, and the lower rotation arm 216 longitudinally aligned with the medial side of the lower leg 230. This configuration can likewise be reversed so that the upper rotation arm 214 is repositioned in longitudinal alignment with the medial side of the lower leg 230 and the lower rotation arm 216 is repositioned in longitudinal alignment with the medial side of the upper leg 228, while the hinge 212 remains aligned with the medial side of the knee joint 232.

Figure 14B:
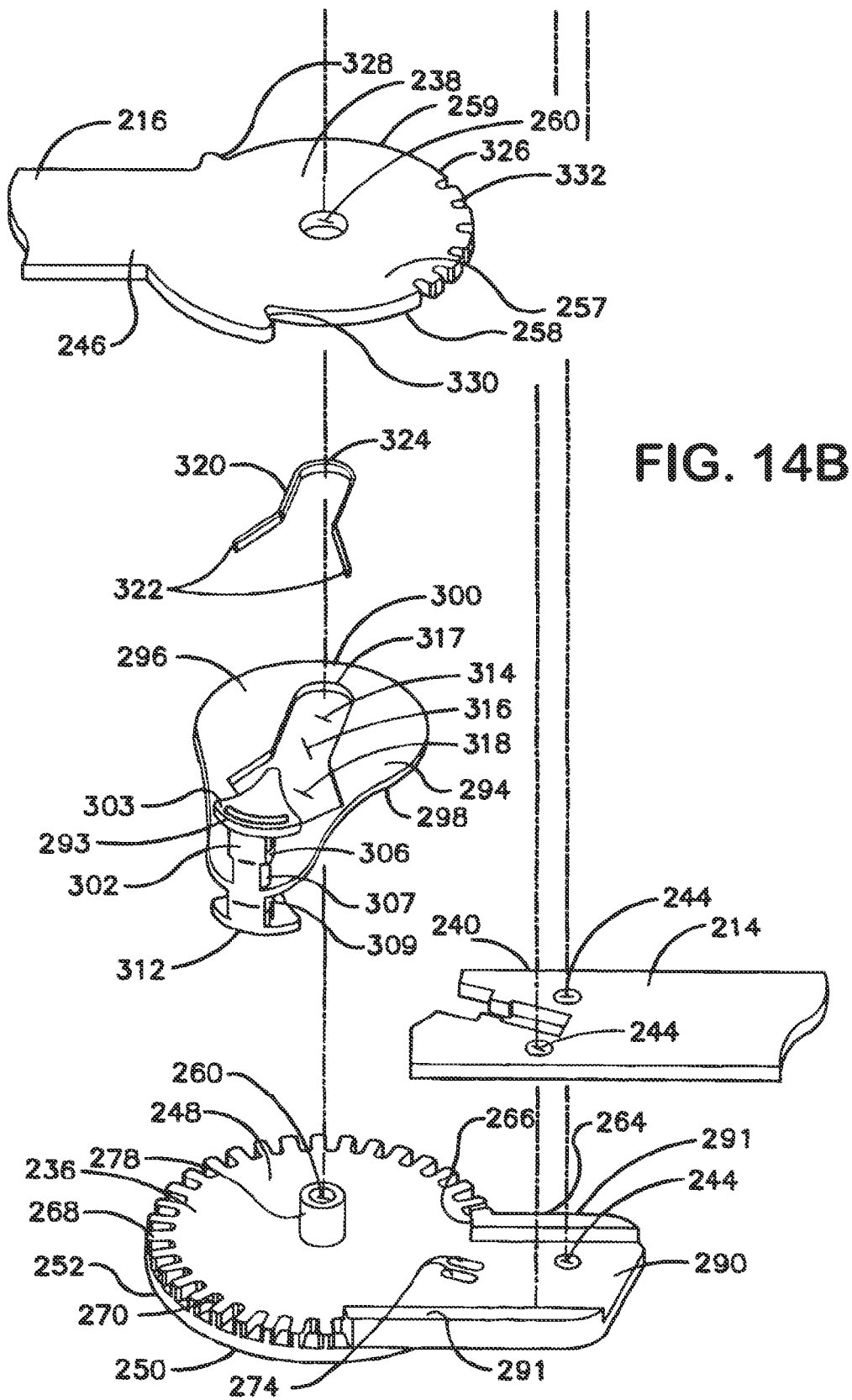

Referring additionally to FIGS. 14A and 14B, the hinge 212 comprises a lateral exterior rotation plate 234, a medial exterior rotation plate 236, and an interior rotation plate 238 rotatably positioned between the lateral and medial exterior rotation plates 234, 236. The lateral and medial exterior rotation plates 234, 236 are fixably fastened to a proximal end 240 of the upper rotation arm 214 by conventional fasteners 242, such as rivets or the like, which extend through fastening apertures 244 provided in the exterior rotation plates 234, 236. The interior rotation plate 238 is integral with the lower rotation arm 216, being contiguous with a proximal end 246 of the lower rotation arm 216.

Although not shown, alternate constructions of the rotation plates 234, 236, 238 in association with the rotation arms 214, 216 are within the scope of the present invention. For example, one or both of the lateral and medial exterior rotation plates 234, 236 may be integral with the upper rotation arm 214, while the interior rotation plate 238 is fixably fastened to the lower rotation arm 216. Alternatively, one or both of the lateral and medial exterior rotation plates 234, 236 may be integral with the upper rotation arm 214, while the interior rotation plate 238 is similarly integral with the lower rotation arm 216. In yet another alternative, the interior rotation plate 238 may be fixably fastened to the lower rotation arm 216, while the lateral and medial exterior rotation plates 234, 236 are similarly fixably fastened to the upper rotation arm 214.

Figure 15:
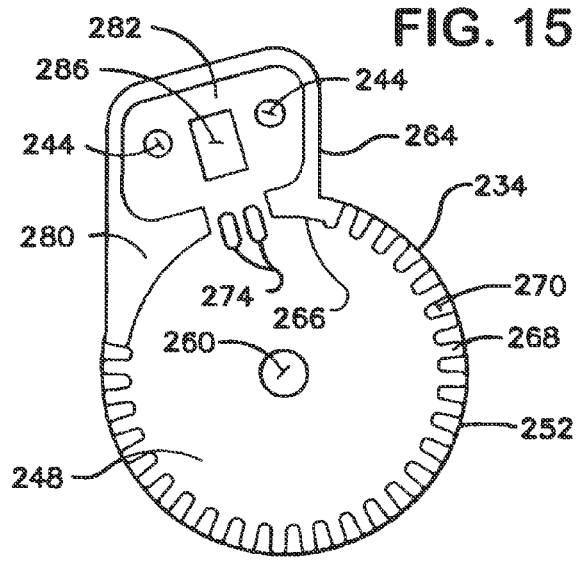
FIG. 15 is a rear view of the inner face of a lateral exterior rotation plate included in the hinge of FIG. 13.

The lateral and medial exterior rotation plates 234, 236 are both preferably formed from a relatively rigid, lightweight, high-strength material, such as a plastic, while the interior rotation plate 238 is preferably formed from the same material as the lower rotation arm 216. Referring additionally to FIG. 15, each exterior rotation plate 234, 236 has a substantially similar circular configuration with an inner face 248 and an outer face 250, which are bounded by a peripheral edge 252. A plurality of flexion rotation limit markers 253, extension rotation limit markers 254, and rotation lock markers 255 are preferably provided on the outer face 250 of the lateral exterior rotation plate 234. A lock reference marker 256 is preferably provided on the proximal end 246 of the lower rotation arm 216.

Each flexion rotation limit marker 253 displays a specific flexion rotation limit value (e.g., 0°, 30°, etc.), which correlates to the flexion angle of the upper and lower rotation arms 214, 216, and correspondingly of the knee joint 232, when the hinge 212 reaches the specific flexion rotation limit corresponding to that value in a manner described hereafter. Each extension rotation limit marker 254 similarly displays a specific extension rotation limit value (e.g., 0°, 30°, etc.), which correlates to the extension angle of the upper and lower rotation arms 214, 216, and correspondingly of the knee joint 232, when the hinge 212 reaches the specific extension rotation limit corresponding to that value in a manner described hereafter. Each rotation lock marker 255 displays a specific lock position value (e.g., 0°, 30°, etc., and further characterized as either flexion or extension), which correlates to the flexion or extension angle of the upper and lower rotation arms 214, 216, and correspondingly of the knee joint 232, when the hinge 212 is locked in the specific lock position corresponding to that value (expressed as a flexion or extension angle) in a manner described hereafter.

The peripheral edge 252 defines the circumference of each exterior rotation plate 234, 236. The inner face 248 of each exterior rotation plate 234, 236 is preferably a smooth, flat, low-friction surface. The interior rotation plate 238 likewise has a substantially circular configuration with a lateral face 257 and a medial face 258, which are bounded by a peripheral edge 259. The peripheral edge 259 defines the circumference of the interior rotation plate 238. The lateral and medial faces 257, 258 of the interior rotation plate 238 are preferably smooth, flat, low-friction surfaces.

Each of the rotation plates 234, 236, 238 is provided with a centrally-positioned pivot aperture 260 extending therethrough. A pivot member 262, having a diameter smaller than the pivot apertures 260, extends through all of the pivot apertures 260 and is fixably, but rotatably, retained therein. As such, the exterior rotation plates 234, 236 are freely rotatable in unison about the pivot member 262 relative to the interior rotation plate 236 when not impeded by the rotation limiting and locking mechanisms of the hinge 212 described hereafter. A preferred pivot member 262 is a rivet having a narrow body and flattened heads at either end, which engage the outer faces 250 of the lateral and medial exterior rotation plates 234, 236, respectively. A bushing (not shown) may also be provided which encloses the body of the pivot member 262 and eases rotation of the rotation plates 234, 236, 238 about the pivot member 262.

Each exterior rotation plate 234, 236 has an integrally-formed fastening extension 264 extending from a segment 266 of the peripheral edge 252. The fastening extension 264 includes the fastening apertures 244 and provides a base for fastening the exterior rotation plates 234, 236 to the proximal end 240 of the upper rotation arm 214 as described above. A plurality of rotation limiting teeth 268 are circumferentially formed at uniform periodically spaced intervals in the inner face 248 of each exterior rotation plate 234, 236 at the peripheral edges 252. The rotation limiting teeth 268 extend in a continuum along the peripheral edge 252 except where the fastening extension 264 extends from the peripheral edge 252.

Each rotation limiting tooth 268 of the lateral exterior rotation plate 234 is aligned at all times with a uniquely corresponding rotation limiting tooth 268 of the medial exterior rotation plate 236 when the hinge 212 is assembled. Furthermore, each rotation limiting tooth 268 of the lateral exterior rotation plate 234 and corresponding rotation limiting tooth 268 of the medial exterior rotation plate 236 is uniquely correlated with a specific flexion or extension rotation limit of the hinge 212. As such, each flexion rotation limit marker 253 displaying a given flexion rotation limit value is uniquely aligned with the rotation limiting tooth 268 correlated with that given flexion rotation limit. Similarly, each extension rotation limit marker 254 displaying a given extension rotation limit value is uniquely aligned with the rotation limiting tooth 268 correlated with that given extension rotation limit.

The rotation limiting teeth 268 each have an identical configuration and are radially aligned relative to the exterior rotation plate 234, 236. Each adjacent pair of rotation limiting teeth 268 on the lateral exterior rotation plate 234 defines a receiving space 270 therebetween and each adjacent pair of rotation limiting teeth 268 on the medial exterior rotation plate 236 likewise defines a receiving space 270 therebetween. Each receiving space 270 of the lateral exterior rotation plate 234 is aligned at all times with a uniquely corresponding receiving space 270 of the medial exterior rotation plate 236 when the hinge 212 is assembled. The rotation limiting teeth 268 and receiving spaces 270 shown herein each has an essentially U-shaped profile, but it is understood that other configurations of the rotation limiting teeth and receiving spaces are possible within the scope of the present invention.

A pair of closely-spaced, side-by-side lock pin slots 274 are also formed in the inner face 248 of each exterior rotation plate 234, 236. Each lock pin slot 274 has an identical closed-ended configuration with an oval shape and each is configured to receive a rotation lock pin 276 in a manner described hereafter. The lock pin slots 274 are positioned at the peripheral edge 252 of each exterior rotation plate 234, 236 along the segment 266 of the peripheral edge 252 from which the fastening extension 264 extends. The lock pin slots 274, like the rotation limiting teeth 268, extend radially relative to the exterior rotation plates 234, 236. Furthermore, each lock pin slot 274 of the lateral exterior rotation plate 234 is aligned at all times with the uniquely corresponding lock pin slot 274 of the medial exterior rotation plate 236 when the hinge 212 is assembled.

Although the exterior rotation plates 234, 236 have a substantially similar construction, as described above, there are some structural distinctions between the lateral and medial exterior rotation plates 234, 236 which facilitate the function of the hinge 212. In particular, the medial exterior rotation plate 236 has an integrally-formed pivot housing 278 positioned on the inner face 248 at the pivot aperture 260. In contrast, the lateral exterior rotation plate 234 is devoid of any additional structure at the pivot aperture 260 so that the inner face 248 of the lateral exterior rotation plate 234 transitions directly into the pivot aperture 260.

The pivot housing 278 is a tubular member which extends away from the inner face 248 about the rotation axis of the medial exterior rotation plate 236. The pivot housing 278 has an open passageway, which is continuous with the pivot aperture 260 of the medial exterior rotation plate 236. The open passageway of the pivot housing 278 also aligns with the pivot aperture 260 of the lateral exterior rotation plate 234. The pivot aperture 260 of the lateral exterior rotation plate 234 is slightly larger than the pivot aperture 260 of the medial exterior rotation plate 236 so that the outer wall of the pivot housing 278 is close-fittingly received into the pivot aperture 260 of the lateral exterior rotation plate 234 when the hinge 212 is assembled.

The configuration of the fastening extensions 264 also differs between the lateral and medial exterior rotation plates 234, 236, respectively. The fastening extension 264 of the lateral exterior rotation plate 234 has an inner face 280 which is raised relative to the remainder of the inner face 248 of the lateral exterior rotation plate 234. The raised inner face 280 includes a transition plate indentation 282 for receiving a lock transition plate 284 therein in a manner described hereafter. An actuator aperture 286 is also provided through the fastening extension 264 of the lateral exterior rotation plate 234, which is positioned between the fastening apertures 244, for receiving a lock actuator assembly 288 therein in a manner described hereafter. In contrast, the fastening extension 264 of the medial exterior rotation plate 236 has an inner face 290 which is relatively level with the remainder of the inner face 248 with the exception of raised rails 291 which extend along the edges of the fastening extension 264 away from the center of the medial exterior rotation plate 236.

Figure 16:
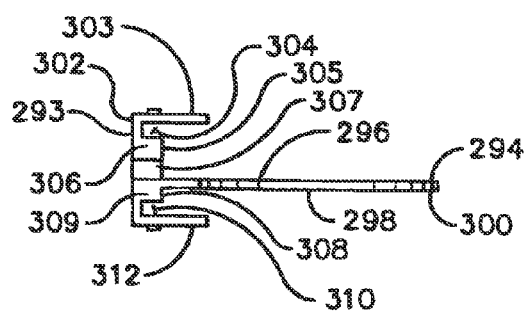
FIG. 16 is a side elevational view of a rotation limiting assembly included in the hinge of FIG. 13.
Figure 17:
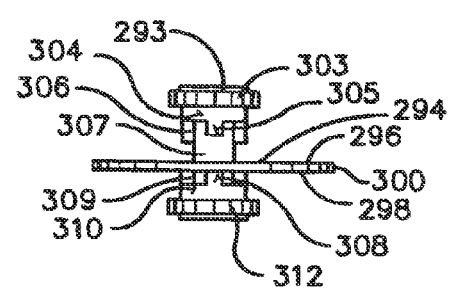
FIG. 17 is a front elevational view of a rotation limiting assembly included in the hinge of FIG. 13.

The rotation limiting mechanism of the hinge 212 includes the rotation limiting teeth 268 and receiving spaces 270 of the exterior rotation plates 234, 236, a flexion rotation limiting assembly 292, an extension rotation limiting assembly 293, and elements of the peripheral edge 259 of the interior rotation plate 238 described hereafter. Referring additionally to FIGS. 16 and 17, the extension rotation limiting assembly 293 comprises a rotation limiting assembly plate 294 having a substantially circular planar configuration with an inner face 296 and an outer face 298 which are bounded by a peripheral edge 300. The peripheral edge 300 defines the circumference of the rotation limiting assembly plate 294, which is preferably smaller than the circumference of the exterior rotation plates 234, 236. The inner and outer faces 296, 298 of the rotation limiting assembly plate 294 are preferably smooth, flat, low-friction surfaces.

The extension rotation limiting assembly 293 further comprises a stop post 302 affixed to the peripheral edge 300 of the rotation limiting assembly plate 294. The longitudinal axis of the stop post 302 is aligned essentially perpendicular to the planar faces 296, 298 of the rotation limiting assembly plate 294. The stop post 302 is serially segmented into a lateral head 303, a lateral stop slot 304, a lateral tooth slot 305 and bounding lateral engagement faces 306, a stop face 307, a medial tooth slot 308 and bounding medial engagement faces 309, a medial stop slot 310, and a medial head 312.

A central portion of the stop post 302 is affixed to the peripheral edge 300 of the rotation limiting assembly plate 294, preferably at the intersection of the stop face 307 and the lateral engagement faces 306 or at the intersection of the stop face 307 and the medial engagement faces 309. As such, the lateral head 303, lateral stop slot 304, lateral tooth slot 305, lateral engagement faces 306, and stop face 307 are on one side of the rotation limiting assembly plate 294, while the medial tooth slot 308, medial engagement faces 309, medial stop slot 310, and medial head 312 are on the opposite side of the rotation limiting assembly plate 294, or alternatively the lateral head 303, lateral stop slot 304, lateral tooth slot 305, and lateral engagement faces 306 are on one side of the rotation limiting assembly plate 294, while the stop face 307, medial tooth slot 308, medial engagement faces 309, medial stop slot 310, and medial head 312 are on the opposite side of the rotation limiting assembly plate 294.

The stop face 307 is defined by a notch formed in the stop post 302 between the lateral and medial engagement faces 306, 309. As such, the stop face 307 has a concave configuration relative to the lateral and medial engagement faces 306, 309. The height of the stop face 307 is preferably slightly greater than the height of the interior rotation plate 238 (i.e., the thickness of the peripheral edge 259) to receive the peripheral edge 259 therein.

The lateral stop slot 304 and peripheral edge 252 of the lateral exterior rotation plate 234 are cooperatively configured so that the lateral stop slot 304 receives a portion of the peripheral edge 252 which is aligned with a receiving space 270. In particular, the lateral stop slot 304 and peripheral edge 252 are configured such that the height of the lateral stop slot 304 is slightly greater than the thickness of the portions of the peripheral edge 252 aligned with the receiving spaces 270. The rotation limiting teeth 268 and lateral tooth slot 305 are cooperatively configured so that a desired rotation limiting tooth 268 fits within the lateral tooth slot 305. The receiving spaces 270 and lateral engagement faces 306 are likewise cooperatively configured so that each lateral engagement face 306 fits within a desired receiving space 270 adjacent to the rotation limiting tooth 268 in the lateral tooth slot 305. The lateral head 303 is manually accessible to a user at a position adjacent to the outer face 250 of the lateral exterior rotation plate 234.

The medial stop slot 310 and peripheral edge 252 of the medial exterior rotation plate 236 are similarly cooperatively configured so that the medial stop slot 310 receives a portion of the peripheral edge 252 which is aligned with a receiving space 270. The rotation limiting teeth 268 and medial tooth slot 308 are cooperatively configured so that a desired rotation limiting tooth 268 fits within the medial tooth slot 308. The receiving spaces 270 and medial engagement faces 309 are likewise cooperatively configured so that each medial engagement face 309 fits within a desired receiving space 270 adjacent to the rotation limiting tooth 268 in the medial tooth slot 308. The medial head 312 is manually accessible to a user at a position adjacent to the outer face 250 of the medial exterior rotation plate 236.

A spring cut-out 314 is formed through the rotation limiting assembly plate 294. The spring cut-out 314 has a relatively narrow central channel 316, which has a closed end 317 and an opposite open end continuous with an adjoining relatively wide peripheral channel 318. The pivot member 262 and pivot housing 278 are received within the central channel 316, the width of the central channel 316 being only slightly greater than the outside diameter of the pivot housing 278. As such, the rotation limiting assembly plate 294 is freely rotatable about the pivot member 262 and pivot housing 278 relative to the rotation plates 234, 236, 238 when not impeded by the rotation limiting and locking mechanisms of the hinge 212. In contrast, the length of the central channel 316 is substantially greater than the outside diameter of the pivot housing 278. As such, the rotation limiting assembly plate 294 is also displaceable in a linear path about the pivot member 262 and pivot housing 278 along the length of the central channel 316 between a fixed position, which enables a rotation mode of operation of the rotation limiting mechanism of the hinge 212, and a rotation limit adjustment position, which enables a rotation limit adjustment mode of operation of the rotation limiting mechanism of the hinge 212, as described hereafter. However, the rotation limiting assembly plate 294 is essentially not linearly displaceable about the pivot member 262 and pivot housing 278 along the width of the central channel 316.

A leaf spring 320 is provided, which is configured to conform to the profile of the spring cut-out 314 and is positioned therein. The leaf spring 320 has two straight end segments 322 joined by a U-shaped middle segment 324. The end segments 322 of the leaf spring 320 engage the walls of the peripheral channel 318, while the middle segment 324 of the leaf spring 320 engages the walls of the central channel 316 and the pivot housing 278. The leaf spring 320 biases the rotation limiting assembly plate 294 in the fixed position. When the rotation limiting assembly plate 294 is in the fixed position, the lateral and medial engagement faces 306, 309 of the stop post 302 are received within correspondingly aligned receiving spaces 270 of the lateral and medial external rotation plates 234, 236 and the rotation limiting teeth 268 are received within correspondingly aligned lateral and medial tooth slots 305, 308. The lateral and medial engagement faces 306, 309 and rotation limiting teeth 268 are retained in their respective positions by the radially-inward directed biasing force of the leaf spring 320. Engagement of the lateral and medial engagement faces 306, 309 and the rotation limiting teeth 268 prevents rotational displacement of the extension rotation limiting assembly 293 about the pivot member 262 relative to the rotation plates 234, 236, 238.

The rotation limiting assembly plate 294 can be transitioned to the rotation limit adjustment position by applying a spring tensioning displacement force to the rotation limiting assembly plate 294 in a radially outward direction aligned with the longitudinal axis of the central channel 316. The displacement force is preferably applied to the rotation limiting assembly plate 294 by manually gripping the lateral and medial heads 303, 312 of the extension rotation limiting assembly 293 and pulling the lateral and medial heads 303, 312 radially outward. When the radially outward displacement force exceeds the biasing force of the leaf spring 320, the displacement force displaces the rotation limiting assembly plate 294 radially outward to withdraw the lateral and medial engagement faces 306, 309 from the receiving spaces 270 and the rotation limiting teeth 268 from the lateral and medial tooth slots 305, 308. As long as a sufficient displacement force is maintained on the rotation limiting assembly plate 294, the rotation limiting assembly plate 294 is retained in the rotation limit adjustment position and the extension rotation limiting assembly 293 is freely rotatable about the pivot member 262 relative to the rotation plates 234, 236, 238. Once the displacement force is withdrawn, the biasing force of the leaf spring 320 returns the rotation limiting assembly plate 294 to the fixed position, which prevents further rotational displacement of the extension rotation limiting assembly 293 about the pivot member 262 relative to the rotation plates 234, 236, 238.

The rotation limiting assembly plate 294 and stop post 302 are preferably integrally formed as a single unitary structure from a relatively rigid, lightweight, high-strength material, such as a plastic, which is the same or similar to that used to form the exterior rotation plates 234, 236. The leaf spring 320 is preferably a separate relatively elastic band formed from a lightweight, high-strength material, such as a malleable metal, e.g., copper.

The flexion rotation limiting assembly 292 is substantially identical to the extension rotation limiting assembly 293 except that the orientation of the flexion rotation limiting assembly 292 is flipped 180° relative to the extension rotation limiting assembly 293 so that both rotation limiting assemblies 292, 293 can be rotated about the pivot member 262 and pivot housing 278 relative to the rotation plates 234, 236, 238 without interfering with one another. Accordingly, the flexion rotation limiting assembly 292 has a rotation limiting assembly plate, stop post and leaf spring which are essentially identical in structure and function to those of the extension rotation limiting assembly 293 described above and, as such, are identified by the same reference characters.

When the hinge 212 is assembled, the inner face 248 of the lateral exterior rotation plate 234 adjoins the outer face 298 of the rotation limiting assembly plate 294 of the flexion rotation limiting assembly 292. The inner face 296 of the rotation limiting assembly plate 294 of the flexion rotation limiting assembly 292 adjoins the lateral face 257 of the interior rotation plate 238. The inner face 248 of the medial exterior rotation plate 236 adjoins the outer face 298 of the rotation limiting assembly plate 294 of the extension rotation limiting assembly 293. The inner face 296 of the rotation limiting assembly plate 294 of the extension rotation limiting assembly 293 adjoins the medial face 258 of the interior rotation plate 238.

Although not shown, the hinge 212 can alternately be assembled so that the inner face 248 of the lateral exterior rotation plate 234 adjoins the outer face 298 of the rotation limiting assembly plate 294 of the extension rotation limiting assembly 293. The inner face 296 of the rotation limiting assembly plate 294 of the extension rotation limiting assembly 293 adjoins the lateral face 257 of the interior rotation plate 238. The inner face 248 of the medial exterior rotation plate 236 adjoins the outer face 298 of the rotation limiting assembly plate 294 of the flexion rotation limiting assembly 292. The inner face 296 of the rotation limiting assembly plate 294 of the flexion rotation limiting assembly 292 adjoins the medial face 258 of the interior rotation plate 238.

The peripheral edge 259 of the interior rotation plate 238 has a rotation arc 326 of about 270°. The rotation arc 326 is bounded on one end by a flexion rotation limiting face 328, which functions in cooperation with the engagement faces 306, 309 of the flexion rotation limiting assembly 292 in a manner described hereafter. The rotation arc 326 is bounded on the opposite end by an extension rotation limiting face 330, which correspondingly functions in cooperation with the engagement faces 306, 309 of the extension rotation limiting assembly 293. The rotation arc 326 additionally has a plurality of lock notches 332 circumferentially formed in the peripheral edge 259 at spaced intervals along the rotation arc intermediately between the flexion and extension rotation limiting faces 328, 330. The lock notches 332 of the interior rotation plate 238 are elements of the rotation locking mechanism, which function in cooperation with the remaining elements of the rotation locking mechanism described hereafter.

Figure 18:
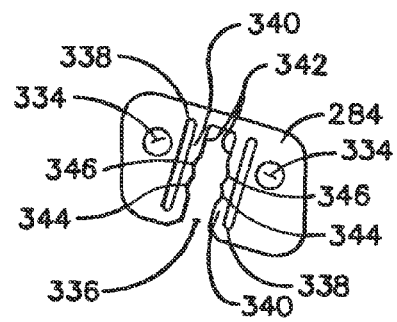
FIG. 18 is a top view of a lock transition plate included in the hinge of FIG. 13.

In addition to the lock notches 332, the rotation locking mechanism of the hinge 212 includes the lock pin slots 274 of the exterior rotation plates 234, 236, the rotation lock pins 276, the lock transition plate 284, and the lock actuator assembly 288. Referring additionally to FIG. 18, the lock transition plate 284 is a planar structure which is sized and configured to nest within the transition plate indentation 282 flush with the inner face 290 of the fastening extension 264 of the medial exterior rotation plate 236. A pair of fastening apertures 334 are formed through the lock transition plate 284, which correspond to the fastening apertures 244 of the exterior rotation plates 234, 236. The fastening apertures 334 are in alignment with the fastening apertures 244 when the hinge 212 is assembled, to receive the fasteners 242 therein. A lock assembly cut-out 336 and a pair of expansion slots 338 are also formed through the lock transition plate 284.

The lock assembly cut-out 336 has an open end, a closed end and two parallel sides. The expansion slots 338 are closely positioned adjacent to the opposite sides of the lock assembly cut-out 336 and are essentially parallely aligned with one another and with the lock assembly cut-out 336. The small separation distance between each expansion slot 338 and the lock assembly cut-out 336 defines an expansion rail 340, which is a narrow strip of relatively flexible material. The edge 342 of each expansion rail 340 bordering the lock assembly cut-out 336 defines the parallel sides of the lock assembly cut-out 336. Each bordering edge 342 has a relatively smooth linear surface with the exception of an arcuately-shaped proximal indentation 344 and an arcuately-shaped distal indentation 346 formed adjacent to one another in the bordering edge 342. The proximal and distal indentations 344, 346 of the opposing bordering edges 342 are positioned in direct corresponding alignment with one another across the lock assembly cut-out 336. The lock transition plate 284 is preferably integrally formed as a single unitary structure from a relatively elastic, lightweight, high-strength material, such as a plastic.

Figure 19:
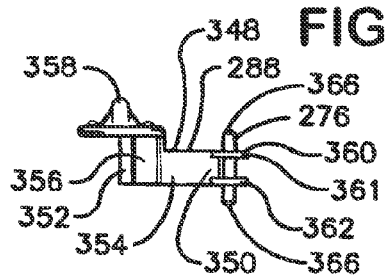
FIG. 19 is a side elevational view of a lock actuator assembly included in the hinge of FIG. 13.
Figure 20:
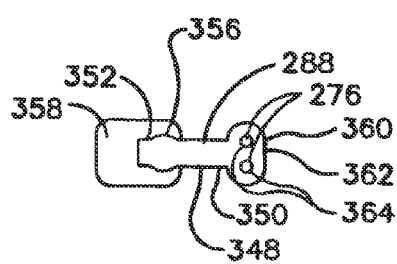
FIG. 20 is a bottom view of a lock actuator assembly included in the hinge of FIG. 13.
Figure 21:
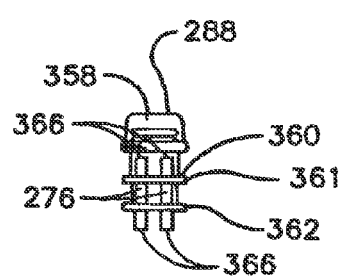
FIG. 21 is a front elevational view of a lock actuator assembly included in the hinge of FIG. 13.

Referring additionally to FIGS. 19-21, the lock actuator assembly 288 comprises an actuator bar 348 having a proximal end 350, a distal end 352, and longitudinal sides 354 connecting the two ends 350, 352. The longitudinal sides 354 have a relatively smooth linear surface with the exception of an arcuate protrusion 356 formed on each longitudinal side 354 of the actuator bar 348 near the distal end 352. Each protrusion 356 is sized and configured in correspondence with the proximal and distal indentations 344, 346 of the lock transition plate 284, so that the contour of the protrusion 356 conforms closely to the contour of either the proximal indentation 344 or the distal indentation 346 when the protrusion 356 is positioned in one of the indentations 344 or 346. The actuator bar 348 is slidably retained in the lock assembly cut-out 336, wherein the longitudinal sides 354 of the actuator bar 348 are essentially parallely aligned with the bordering edges 342 of the expansion rails when the hinge 212 is assembled.

A manually accessible actuator grip 358 is positioned adjacent to the outer face 250 of the lateral exterior rotation plate 234 and is connected to the distal end 352 of the actuator bar 348 through the actuator aperture 286 of the lateral exterior rotation plate 234. A lock pin retainer 360 is mounted on the proximal end 350 of the actuator bar 348. The lock pin retainer 360 includes a lateral pin retainer plate 361 and a medial pin retainer plate 362 positioned one atop the other and spaced a distance apart, which corresponds approximately to the thickness of the interior rotation plate 238. Each pin retainer plate 361, 362 has a pair of side-by-side pin apertures 364 formed therethrough and spaced a distance apart, which corresponds to the distance between the closely-spaced lock pin slots 274. Accordingly, there are a total of four pin apertures 364, two in the lateral pin retainer plate 361 and two in the medial pin retainer plate 362.

One of the two rotation lock pins 276 is fixably mounted within the two pin apertures 364 aligned one atop the other in the two pin retainer plates 361, 362 and the remaining rotation lock pin 276 is fixably mounted within the remaining two vertically-aligned pin apertures 364. The ends 366 of each rotation lock pin 276 extend beyond the pin retainer plates 361, 362. One extended end 366 of each rotation lock pin 276 is slidably positioned in the adjoining lock pin slots 274 of the lateral exterior rotation plate 234 when the hinge 212 is assembled and the opposite extended end 366 of each rotation lock pin 276 is slidably positioned in the adjoining lock pin slots 274 of the medial exterior rotation plate 236. Each lock pin slot 274 and rotation lock pin 276 has a longitudinal axis. The longitudinal axes of the rotation lock pins 276 are aligned perpendicular to the inner faces of the 248 of the lateral and medial exterior rotation plates 234, 236 and are likewise aligned perpendicular to the longitudinal axes of the lock pin slots 274.

The actuator bar 348, actuator grip 358, and pin retainer plates 361, 362 are preferably integrally formed as a single unitary structure from a relatively rigid, lightweight, high-strength material, such as a plastic, which is the same or similar to that used to form the exterior rotation plates 234, 236 and rotation limiting assemblies 292, 293. The rotation lock pins 276 are preferably separate relatively rigid rods formed from a lightweight, high-strength material, such as a metal, e.g. steel or aluminum. The rotation lock pins 276 are sized and configured to be received within the lock notches 332 on the peripheral edge 259 of the interior rotation plate 238. Operation of the rotation locking mechanism is effected by the positioning of the rotation lock pins 276 relative to the lock notches 332. In particular, placement of the rotation lock pins 276 and lock notches 332 in an unlocked position, wherein the rotation lock pins 276 are radially separated from the adjacent lock notches 332, enables an unlocked mode of operation of the rotation locking mechanism. Placement of the rotation lock pins 276 and lock notches 332 in a locked position, wherein the rotation lock pins 276 are fitted within adjacent lock notches 332, enables a locked mode of operation of the rotation locking mechanism.

Method of Operation

Figure 22:
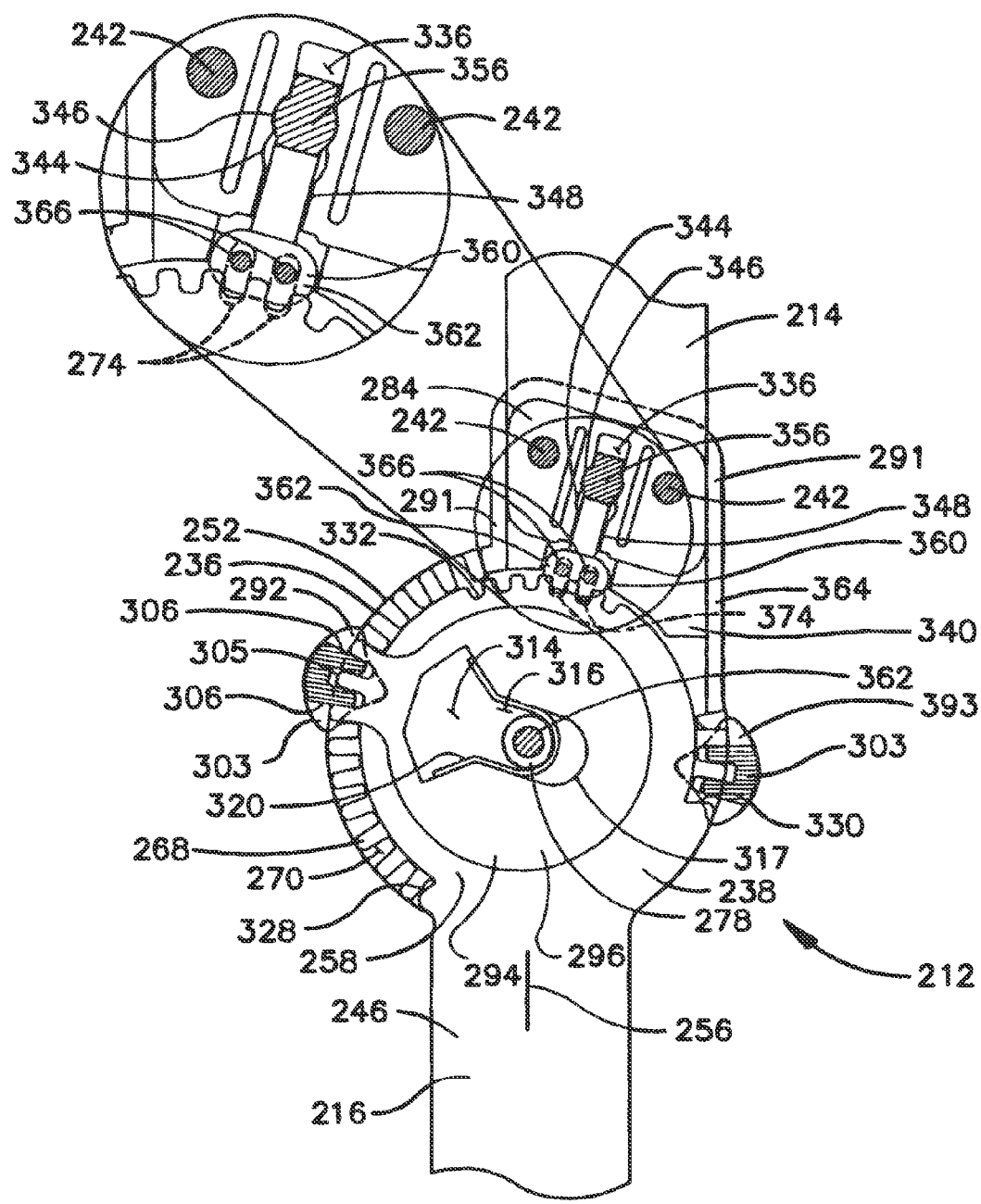
FIG. 22 is a cutaway frontal view of the hinge of FIG. 13, wherein a rotation limiting mechanism of the hinge is in a rotation mode of operation and a rotation locking mechanism of the hinge is in an unlocked mode of operation.

The modes of operation of the above-described hinge 212 and the corresponding positions of the hinge components are described hereafter with reference to the Figures. Referring initially to FIG. 22 in association with FIGS. 13-21, the rotation limiting mechanism of the hinge 212 is shown in the rotation mode of operation and the rotation locking mechanism of the hinge 212 is shown in the unlocked mode of operation. For clarity, the lateral exterior rotation plate 234, actuator grip 358 and lateral pin retainer plate 361 have been removed from the hinge 212 in the view of FIG. 22.

In accordance with the rotation mode of operation, the flexion and extension rotation limiting assemblies 292, 293 are in the fixed position. More particularly, with specific reference to the flexion rotation limiting assembly 292, the rotation mode of operation comprises rotatably positioning the pivot housing 278 of the medial exterior rotation plate 236, which encloses the pivot member 262, within the central channel 316 of the spring cut-out 314 in the rotation limiting assembly plate 294 of the flexion rotation limiting assembly 292 such that the pivot housing 278 is spaced a distance away from the closed end 317.

The rotation mode of operation further comprises fitting a portion of the peripheral edge 252 aligned with a receiving space 270 of the medial exterior rotation plate 236 within the lateral stop slot 304 of the flexion rotation limiting assembly 292, fitting a desired rotation limiting tooth 268 of the medial exterior rotation plate 236 within the lateral tooth slot 305 of the flexion rotation limiting assembly 292, and fitting the lateral engagement faces 306 of the flexion rotation limiting assembly 292 within the receiving spaces 270 of the medial exterior rotation plate 236 adjacent to the rotation limiting tooth 268 in the lateral tooth slot 305. In addition, the lateral head 303 of the flexion rotation limiting assembly 292 is positioned adjacent to the outer face 250 of the medial exterior rotation plate 236. The biasing force of the leaf spring 320 maintains the position of the rotation limiting assembly plate 294 fixed relative to the pivot member 262 and pivot housing 278 preventing inadvertent repositioning of the rotation limiting assembly plate 294 during the rotation mode of operation.

Although not shown in FIG. 22, the rotation mode of operation further comprises fitting a portion of the peripheral edge 352 aligned with the corresponding receiving space 270 of the lateral exterior rotation plate 234 within the medial stop slot 310 of the flexion rotation limiting assembly 292, fitting the corresponding rotation limiting tooth 268 of the lateral exterior rotation plate 234 within the lateral tooth slot 305 of the flexion rotation limiting assembly 292, and fitting the lateral engagement faces 306 of the flexion rotation limiting assembly 292 within the corresponding receiving spaces 270 of the lateral exterior rotation plate 234. In addition, the medial head 312 is positioned adjacent to the outer face 250 of the lateral exterior rotation plate 234. Only the lateral head 303 of the extension rotation limiting assembly 293 is shown in FIG. 22. However, it is understood that the components of the extension rotation limiting assembly 293, which correspond to like components of the flexion rotation limiting assembly 292, are positioned in a substantially similar manner to the above description relating to the flexion rotation limiting assembly 292.

In accordance with the unlocked mode of operation, the lock actuator assembly 288 is in a distal or unlocked position. More particularly, the unlocked mode of operation comprises placing the actuator grip 358 connected to the distal end 352 of the actuator bar 348 at a distal position adjacent to the outer face 250 of the lateral exterior rotation plate 234. Distal positioning of the actuator grip 358 concurrently positions the extended ends 366 of the rotation lock pins 276 mounted within the lock pin retainer 360 at the proximal end 350 of the actuator bar 348 toward the distal end of the lock pin slots 274 in the medial exterior rotation plate 236. Although not shown, it is understood that the extended ends 366 of the rotation lock pins 276 are also positioned toward the distal end of the lock pin slots 274 in the lateral exterior rotation plate 234.

The above-recited distal positions of the actuator grip 358 and rotation lock pins 276 are maintained by tightly fitting the protrusions 356 on the longitudinal sides 354 of the actuator bar 348 near the distal end 352 into the distal indentation 346 along the bordering edges 342 of the lock assembly cut-out 336 in the lock transition plate 284 to inhibit inadvertent slidable displacement of the actuator bar 348 and the associated actuator grip 358 and rotation lock pins 276 during the unlocked mode of operation. The effect of distally positioning the actuator grip 358 and rotation lock pins 276 as recited above is to radially separate the rotation lock pins 276 a sufficient distance from the lock notches 332 in the peripheral edge 259 of the interior rotation plate 238 so that the rotation locking mechanism does not substantially impede the rotation mode of operation of the rotation limiting mechanism, when the rotation locking mechanism is in the unlocked mode of operation. It is further noted that the medial pin retainer plate 362 is medially positioned essentially clear of the peripheral edge 259 of the interior rotation plate 238 and the lateral pin retainer plate 361 (not shown in FIG. 22) is laterally positioned essentially clear of the peripheral edge 259 so that neither pin retainer plate 361, 362 impedes rotation of the hinge 212 at any time during hinge operation.

Figure 23:
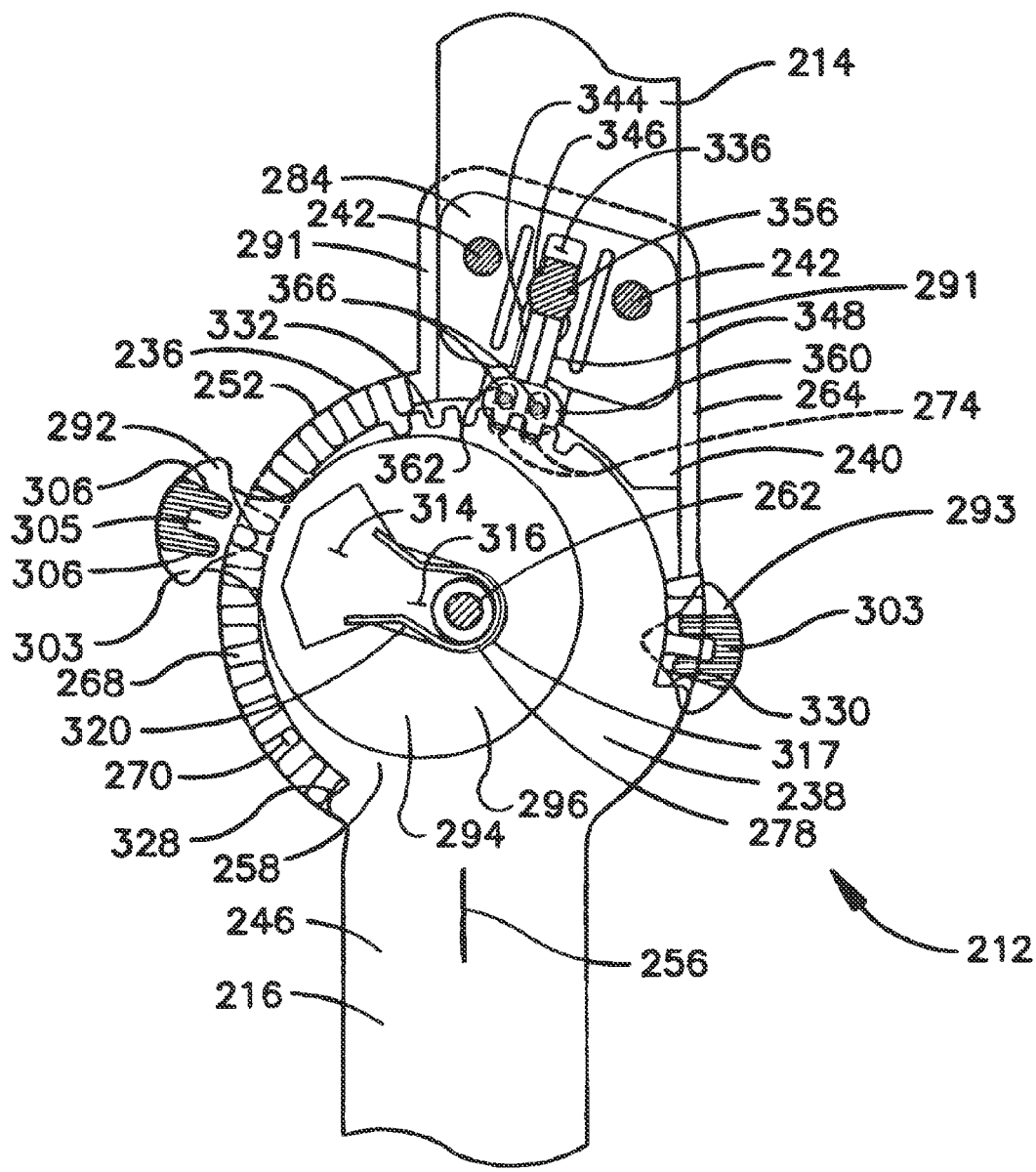
FIG. 23 is a cutaway frontal view of the hinge of FIG. 13, wherein the rotation limiting mechanism is in a rotation limit adjustment mode of operation and the rotation locking mechanism is in the unlocked mode of operation.

Referring to FIG. 23, the rotation limiting mechanism of the hinge 212 is shown in the rotation limit adjustment mode of operation, while the rotation locking mechanism of the hinge 212 is shown in the unlocked mode of operation. In accordance with the present depiction of the rotation limit adjustment mode of operation, the extension rotation limiting assembly 293 remains in the fixed position, while the flexion rotation limiting assembly 292 has been transitioned to the rotation limit adjustment position. However, it is readily apparent to the skilled artisan from the following description that the rotation limit adjustment mode of operation further encompasses transitioning the extension rotation limiting assembly 293 to the rotation limit adjustment position while the flexion rotation limiting assembly 292 remains in the fixed position or transitioning both the flexion and extension rotation limiting assemblies 292, 293 to the rotation limit adjustment position simultaneously. It is also apparent that the rotation locking mechanism of the hinge 212 can alternatively be in the locked mode of operation described hereafter, when the rotation limiting mechanism of the hinge 212 is in the rotation limit adjustment mode of operation.

With specific reference to the flexion rotation limiting assembly 292, the rotation limit adjustment mode of operation comprises displacing the rotation limiting assembly plate 294 of the flexion rotation limiting assembly 292 radially outward by applying a radially outward directed manual force to the lateral head 303 to overcome the biasing force of the leaf spring 320. The leaf spring 320 is increasingly tensioned as the closed end 317 of the central channel 316 of the spring cut-out 314 in the rotation limiting assembly plate 294 of the flexion rotation limiting assembly 292 is displaced toward the pivot housing 278 of the medial exterior rotation plate 236. At the same time, the lateral engagement faces 306 are radially withdrawn from the receiving spaces 270 and the corresponding rotation limiting tooth 268 is radially withdrawn from the lateral tooth slot 305. Transitioning the flexion rotation limiting assembly 292 to the rotation limit adjustment position enables rotation of the flexion rotation limiting assembly 292 about the pivot member 262 and pivot housing 278.

Although not shown in FIG. 23, the rotation limit adjustment mode of operation may additionally or alternatively comprise displacing the rotation limiting assembly plate 294 of the flexion rotation limiting assembly 292 radially outward by applying a radially outward directed manual force to the medial head 312 to overcome the biasing force of the leaf spring 320. Increasingly tensioning the leaf spring 320 and displacing the closed end 317 of the central channel 316 toward the pivot housing 278 also simultaneously radially withdraws the medial engagement faces 309 from the corresponding receiving spaces 270 and the corresponding rotation limiting tooth 268 from the medial tooth slot 308.

Figure 24:
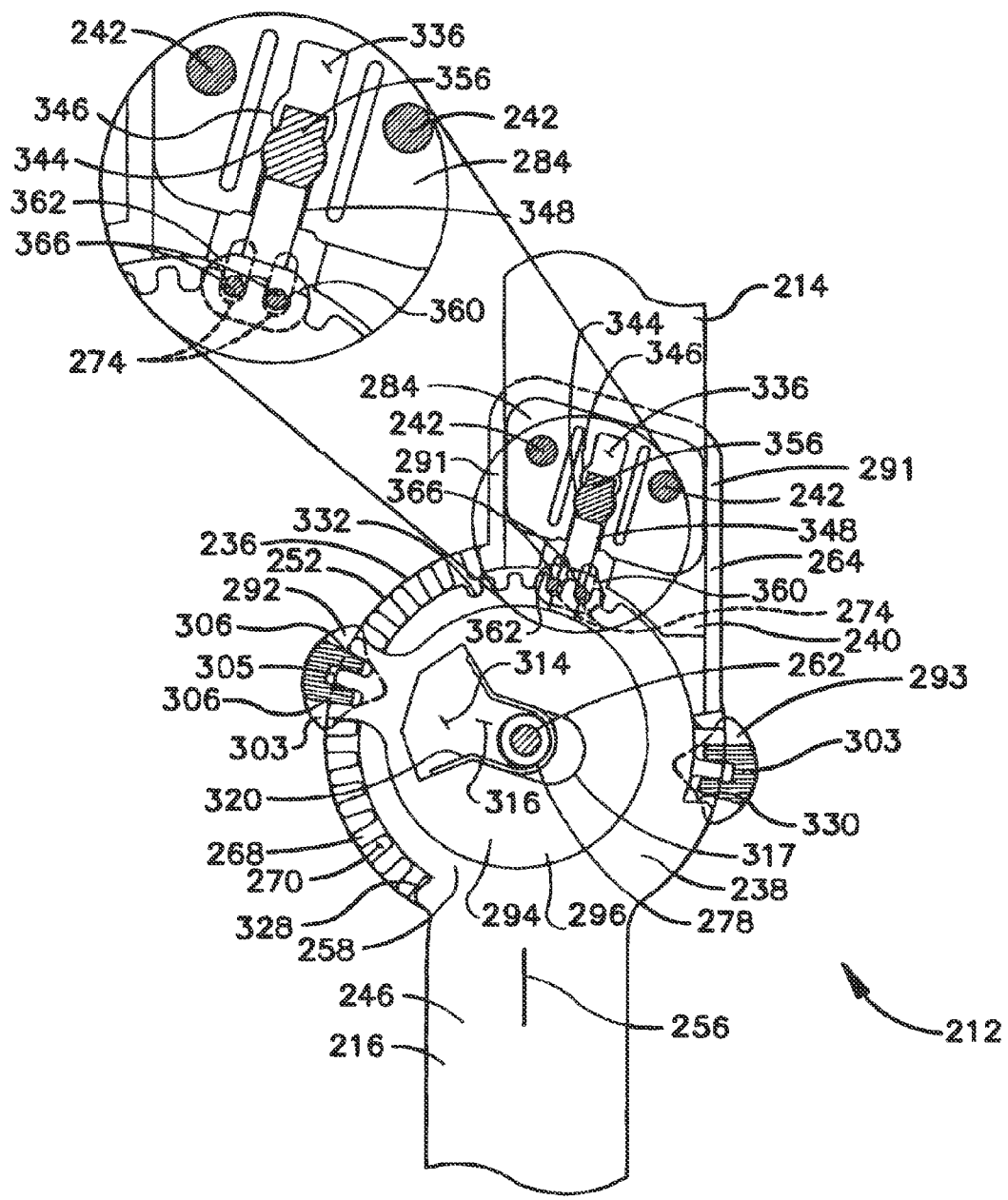
FIG. 24 is a cutaway frontal view of the hinge of FIG. 13, wherein the rotation limiting mechanism is in the rotation mode of operation and the rotation locking mechanism is in a locked mode of operation.

Referring to FIG. 24, the rotation limiting mechanism of the hinge 212 is shown in the rotation mode of operation, while the rotation locking mechanism of the hinge 212 is shown in the locked mode of operation. In accordance with the locked mode of operation, the lock actuator assembly 288 is transitioned from the distal or unlocked position to a proximal or locked position. More particularly, the locked mode of operation comprises manually gripping the actuator grip 358 and slidably displacing the actuator grip 358 in a radially inward direction from the distal position to a proximal position which is likewise adjacent to the outer face 250 of the lateral exterior rotation plate 234. Displacement of the actuator grip 358 is enabled by applying a manual displacement force to the actuator grip 358 which is sufficient to cause the protrusions 356 to press against the bordering edges 342 of the lock assembly cut-out 336 in the lock transition plate 284 and bow the expansion rails 340 outward in cooperation with the expansion slots 338. This provides sufficient clearance for the protrusions 356 to slide out of the distal indentation 346 and travel inwardly through the lock assembly cut-out 336 to the proximal indentation 344.

Displacement of the actuator grip 358 concurrently effects slidable displacement of the extended ends 366 of the rotation lock pins 276 in a radially inward direction toward the proximal end of the lock pin slots 274 in the lateral and medial exterior rotation plates 234, 236. The above-recited proximal positions of the actuator grip 358 and rotation lock pins 276 are maintained by tightly fitting the protrusions 356 on the actuator bar 348 into the proximal indentation 344 to inhibit inadvertent slidable displacement of the actuator bar 348 and the associated actuator grip 358 and rotation lock pins 276 during the locked mode of operation. The effect of proximally positioning the actuator grip 358 and rotation lock pins 276 as recited above is to engage the rotation lock pins 276 within the lock notches 332 in the peripheral edge 259 of the interior rotation plate 238 so that the rotation locking mechanism substantially prevents the rotation mode of operation of the rotation limiting mechanism, when the rotation locking mechanism is in the locked mode of operation.

The rotation locking mechanism enables the practitioner to select a desired locking point for the hinge 212 having a specific degree of rotation from a range of available locking points. The selected locking point is indicated by alignment of the lock reference marker 256 on the proximal end 246 of the lower rotation arm 216 with the selected rotation lock marker 256 on the outer face 250 of the lateral exterior rotation plate 234. An exemplary range of locking points available for selection is between −10° and 30° of extension, wherein the sequential locking points are at graduated intervals of 10°.

Figure 25:
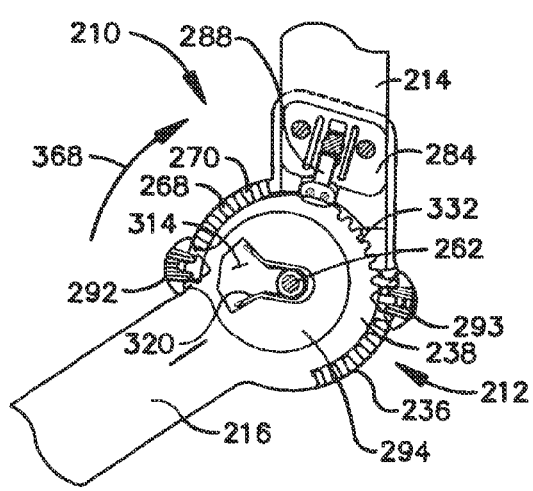
FIG. 25 is a cutaway frontal view of the hinge of FIG. 13, wherein the rotation limiting mechanism is in the rotation mode of operation and the rotation locking mechanism is in the unlocked mode of operation and further wherein the hinge is rotated in a clockwise direction to a preselected first flexion rotation limit.

The modes of operation of the rotation limiting and locking mechanisms of the hinge 212 are further described hereafter by way of example with reference to FIGS. 25-28. Referring initially to FIG. 25 in association with FIGS. 13-24, the rotation limiting mechanism is in the rotation mode of operation. The lower rotation arm 216 of the brace 210 is rotated about the hinge 212 in a first direction of rotation, which is clockwise as indicated by the arrow 368, until the hinge 212 reaches a preselected first flexion rotation limit where the flexion rotation limiting face 328 on the peripheral edge 259 of the interior rotation plate 238 engages the stop face 307 on the flexion rotation limiting assembly 292. The first flexion rotation limit is preselected in accordance with the rotation limit adjustment mode of operation described above. In the example of FIG. 25, the first flexion rotation limit is 60° as indicated by alignment of the lateral head 303 of the flexion rotation limiting assembly 292 with the 60° flexion rotation limit marker 253 on the outer face 250 of the lateral exterior rotation plate 234. An exemplary range of flexion rotation limits available for selection is between −10° and 120°, wherein the sequential flexion rotation limits are at graduated intervals of 10°.

As noted above, each rotation limiting tooth 268 on the lateral exterior rotation plate 234 is uniquely correlated with a specific flexion or extension rotation limit of the hinge 212 and each flexion rotation limit marker 253 on the lateral exterior rotation plate 234 is aligned with the unique rotation limiting tooth 268 correlated with the flexion rotation limit value displayed by the marker 253. Thus, for example, when the lateral head 303 of the flexion rotation limiting assembly 292 is aligned with the flexion rotation limit marker 253 displaying a flexion rotation limit value of 60°, the rotation limiting tooth 268 correlated with the 60° flexion rotation limit is fitted in the lateral tooth slot 305 of the flexion rotation limiting assembly 292, and the hinge 212 is rotated to 60° flexion, the flexion rotation limiting face 328 on the peripheral edge 259 of the interior rotation plate 238 engages the stop face 307 of the flexion rotation limiting assembly 292.

Figure 26:
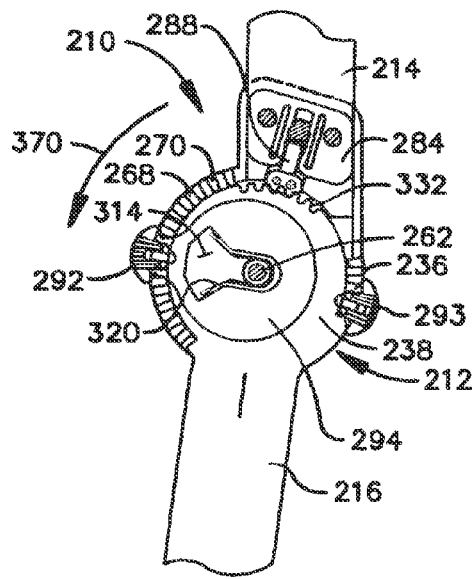
FIG. 26 is a cutaway frontal view of the hinge of FIG. 13, wherein the rotation limiting mechanism is in the rotation mode of operation and the rotation locking mechanism is in the unlocked mode of operation and further wherein the hinge is rotated in a counterclockwise direction to a preselected first extension rotation limit.

Referring to FIG. 26, the rotation limiting mechanism remains in the rotation mode of operation. The lower arm 216 of the brace 210 is rotated about the hinge 212 in a second direction of rotation, which is counterclockwise as indicated by the arrow 370, until the hinge 212 reaches a preselected first extension rotation limit where the extension rotation limiting face 330 on the peripheral edge 259 of the interior rotation plate 238 engages the stop face 307 on the extension rotation limiting assembly 293. The first extension rotation limit is likewise preselected in accordance with the rotation limit adjustment mode of operation described above. In the example of FIG. 26, the first extension rotation limit is 10° as indicated by alignment of the lateral head 303 of the extension rotation limiting assembly 293 with the 10° extension rotation limit marker 254 on the outer face 250 of the lateral exterior rotation plate 234. An exemplary range of extension rotation limits available for selection is between −10° and 30°, wherein the sequential extension rotation limits are at graduated intervals of 10°.

As noted above, each rotation limiting tooth 268 on the lateral exterior rotation plate 234 is uniquely correlated with a specific flexion or extension rotation limit of the hinge 212 and each extension rotation limit marker 254 on the lateral exterior rotation plate 234 is aligned with the unique rotation limiting tooth 268 correlated with the extension rotation limit value displayed by the marker 254. Thus, for example, when the lateral head 303 of the extension rotation limiting assembly 293 is aligned with the extension rotation limit marker 254 displaying an extension rotation limit value of 10°, the rotation limiting tooth 268 correlated with the 10° extension rotation limit is fitted in the lateral tooth slot 305 of the extension rotation limiting assembly 293, and the hinge 212 is rotated to 10° extension, the extension rotation limiting face 330 on the peripheral edge 259 of the interior rotation plate 238 engages the stop face 307 of the extension rotation limiting assembly 293.

It is further noted with reference to FIG. 26 that each pair of lock notches 332 on the peripheral edge 259 of the interior rotation plate 238 is uniquely correlated with a specific lock position of the hinge 212. In addition, the position of each rotation lock marker 255 relative to the rotation lock pins 276 is likewise uniquely correlated with a specific lock position of the hinge 212. Thus, for example, when the hinge 212 is rotated to 10° extension, the rotation lock marker 255 displaying a lock position value of 10° extension is aligned with the lock reference marker 256 on the lower rotation arm 216 and the rotation lock pins 276 are aligned with the pair of lock notches 332 correlated with a lock position corresponding to 10° extension. Once this alignment of the rotation lock marker 255, lock reference marker 256, rotation lock pins 276, and pair of lock notches 332 is achieved, the rotation locking mechanism can be transitioned to the locked mode of operation in the manner described above.

It is apparent that the elements of the rotation locking mechanism are structurally distinct from the elements of the rotation limiting mechanism. Thus, none of the structural elements of the rotation locking mechanism are employed in the operation of the rotation limiting mechanism and vice versa. As a result, the lock position of the hinge 212 can be selected independent of the flexion and extension rotation limits of the hinge 212 as long as the selected value of the lock position is less than or equal to the value of the flexion or extension rotation limit. This is an advantageous feature of the present hinge because in most cases the practitioner is able to select the value of the lock position without changing the value of the flexion or extension rotation limit.

Figure 27:
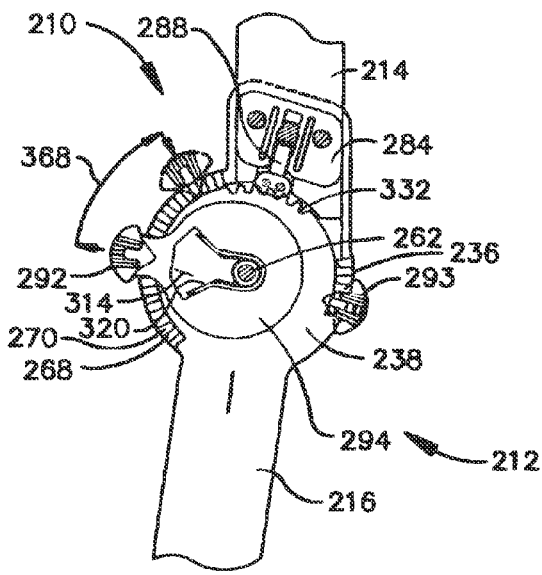
FIG. 27 is a cutaway frontal view of the hinge of FIG. 25, wherein the rotation limiting mechanism is in the rotation limit adjustment mode of operation and the rotation locking mechanism is in the unlocked mode of operation and further wherein the flexion rotation limit of the hinge is being adjusted from the first flexion rotation limit of FIG. 25 to a second flexion rotation limit.

Referring to FIG. 27, the rotation limiting mechanism is transitioned to the rotation limit adjustment mode of operation, wherein the preselected first flexion rotation limit of FIG. 25 is adjusted to a second flexion rotation limit in the clockwise direction of the arrow 368 in accordance with the rotation limit adjustment mode of operation described above. In the example of FIG. 27, the second flexion rotation limit is 110° as indicated by alignment of the lateral head 303 of the flexion rotation limiting assembly 292 with the 110° flexion rotation limit marker 253 on the outer face 250 of the lateral exterior rotation plate 234. Adjustment of the extension rotation limit can also be performed in a like manner to the above-described adjustment of the flexion rotation limit, as is readily apparent to the skilled artisan. Upon completion of the rotation limit adjustment mode of operation, operation of the rotation limiting mechanism is resumed in the rotation mode with the hinge 212 having an adjusted flexion and/or extension rotation limit.

Figure 28:
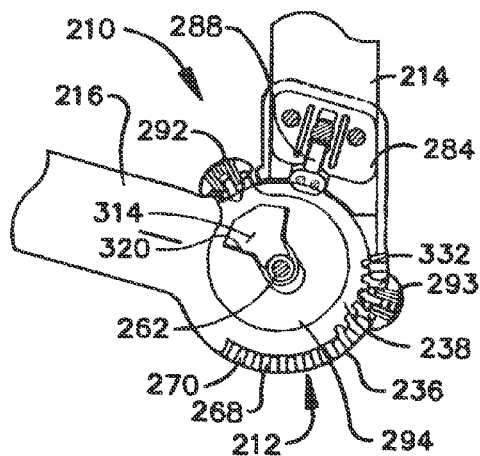
FIG. 28 is a cutaway frontal view of the hinge of FIG. 13, wherein the rotation limiting mechanism is in the rotation mode of operation and the rotation locking mechanism is in the unlocked mode of operation and further wherein the hinge is rotated in the clockwise direction to the second flexion rotation limit of FIG. 27.

Referring to FIG. 28, the rotation limiting mechanism resumes the rotation mode of operation. The lower arm 216 of the brace 210 is rotated about the hinge 212 until the hinge 212 reaches the second flexion rotation limit selected in accordance FIG. 27 where the flexion rotation limiting face 328 on the peripheral edge 259 of the interior rotation plate 238 again engages the stop face 307 on the flexion rotation limiting assembly 292 in substantially the same as described above with reference to FIG. 25.

While the forgoing preferred embodiments of the invention have been described and shown, it is understood that alternatives and modifications, such as those suggested and others, may be made thereto and fall within the scope of the invention. For example, the hinge 212 has been described above as having a pair of rotation lock pins 276 and a pair of rotation limiting assemblies 292, 293. However, a hinge having only a single rotation lock pin and/or a single rotation limiting assembly is alternatively within the purview of the skilled artisan and within the scope of the present invention. The hinge 212 has also been described above as having a pair of external rotation plates 234, 236 and an internal rotation plate 238. However, a hinge having only a single external rotation plate and internal rotation plate is alternatively within the purview of the skilled artisan and within the scope of the present invention. It is likewise readily apparent to the skilled artisan to modify or eliminate elements of the hinge, which are cooperative with the eliminated external rotation plate, rotation limiting assembly and/or rotation lock pin of the alternate embodiments. For example, the flexion and/or extension rotation limiting assemblies 292, 293, rotation lock pins 276, or lock actuator assembly 288 can be modified to accommodate such alternate embodiments.

A hinge having two external rotation plates and a single internal rotation plate, but wherein only one of the external rotation plates includes the rotation limiting teeth 268, receiving spaces 270, and/or lock pin slots 274, is alternatively within the purview of the skilled artisan and within the scope of the present invention. In accordance with these alternate embodiments, one external rotation plate can include the rotation limiting teeth 268, receiving spaces 270, and lock pin slots 274, thereby supporting both the rotation limiting and rotation locking functions of the hinge, while the other external rotation plate is devoid of rotation limiting teeth, receiving spaces, and lock pin slots, thereby supporting neither the rotation limiting function nor the rotation locking function of the hinge. Alternatively, one external rotation plate can include the rotation limiting teeth 268 and receiving spaces 270, but not the lock pin slots 274, thereby only supporting the rotation limiting function of the hinge, while the other external rotation plate includes the lock pin slots 274, but not the rotation limiting teeth 268 and receiving spaces 270, thereby only supporting the rotation locking function of the hinge.

While the forgoing preferred embodiments of the invention have been described and shown, it is understood that alternatives and modifications, such as those suggested and others, may be made thereto and fall within the scope of the invention.

We claim:

1. A method for setting a rotation limit on a hinge for an orthopedic brace and for transitioning the hinge between a rotation locked position to lock the hinge against rotation and a rotation unlocked position to permit rotation of the hinge within the rotation limit, the method comprising:
   providing a hinge including a first rotation plate having a first peripheral edge, a second rotation plate having a second peripheral edge, a pivotal connector connecting said first and second rotation plates, and a rotation limiting mechanism having a series of rotation limiting teeth proximate said first peripheral edge, a rotation limiting face proximate said second peripheral edge, and a rotation limiter;

selectively positioning said rotation limiter with respect to said series of teeth to set said rotation limiter at a rotation limitation point;

engaging said rotation limiting face with said rotation limiter upon rotation of said second rotation plate relative to said first rotation plate in a first rotation direction opposite a second rotation direction to substantially prevent rotation of said second rotation plate in said first rotation direction past said rotation limiter at said rotation limitation point;

further providing said hinge with a rotation locking mechanism including, a series of lock notches proximate said second peripheral edge, a rotation lock member, a lock actuator connected to said rotation lock member and having a lock actuator width, a pair of edges spaced a distance apart in opposing alignment with one another across a displacement channel slidably receiving said lock actuator, wherein at least one of said edges is formed by an expansion rail and said displacement channel is substantially radially fixed relative to said pivotal connector, said distance apart has a narrowed point less than said lock actuator width, and said narrowed point defines a first side on one side of said narrowed point and a second side on an opposing side of said narrowed point;

selectively positioning said rotation lock member at a rotation locked position with respect to said series of lock notches, thereby selectively substantially locking said first and second rotation plates against rotation relative to one another in said first and second rotation directions;

selectively positioning said rotation lock member at a rotation unlocked position with respect to said series of lock notches, thereby selectively substantially permitting rotation of said first and second rotation plates relative to one another in said first and second rotation directions;

radially slidably displacing said lock actuator and said rotation lock member relative to said pivotal connector to transition said rotation lock member between said rotation locked position and said rotation unlocked position;

engaging and elastically displacing said expansion rail at said narrowed point with said lock actuator to widen said narrowed point when radially slidably displacing said lock actuator relative to said pivotal connector through said narrowed point between said first side and said second side of said narrowed point, wherein positioning said lock actuator on said first side enables said rotation locked position of said rotation lock member and positioning said lock actuator on said second side enables said rotation unlocked position of said rotation lock member.

2. The method of claim 1 further comprising biasing said rotation limiter radially with respect to said first peripheral edge.

3. The method of claim 1 wherein said rotation lock member is transitioned between said rotation locked position and said rotation unlocked position without substantially displacing said rotation limiter from said rotation limitation point.

4. The method of claim 1 wherein said displacement channel is substantially radially fixed relative to said first rotation plate.

5. The method of claim 1 wherein said displacement channel is substantially rotationally fixed relative to said first rotation plate when said rotation lock member is in said rotation unlocked position.

6. The method of claim 1 wherein said displacement channel is substantially rotationally displaceable relative to said second rotation plate when said rotation lock member is in said rotation unlocked position.

7. An orthopedic brace comprising:
a first rotation arm;
a second rotation arm;
a pivot enabling rotational displacement of said first and second rotation arms relative to one another about said pivot in a first rotation direction or a second rotation direction opposite said first rotation direction;
a first rotation limiter selectively positionable with respect to one of said first and second rotation arms to prevent rotation of said second rotation arm about said pivot in said first rotation direction past a first rotation limitation point while substantially permitting rotation of said second rotation plate in said second rotation direction;
a second rotation limiter selectively positionable with respect to one of said first and second rotation arms to prevent rotation of said second rotation arm about said pivot in said second rotation direction past a second rotation limitation point while substantially permitting rotation of said second rotation plate in said first rotation direction, said first and second rotation limiters in combination defining a limited rotation range of said first and second rotation arms relative to one another about said pivot in said first and second rotation directions between said first and second rotation limitation points; and
a rotation lock member selectively positionable at a rotation lock point to achieve a rotation locked position substantially locking said first and second rotation arms against rotation relative to one another in said first and second rotation directions.

8. The brace of claim 7 wherein said rotation lock member is selectively positioned at said rotation lock point while maintaining said first rotation limiter positioned to prevent rotation of said second rotation arm past said first rotation limitation point and while maintaining said second rotation limiter positioned to prevent rotation of said second rotation arm past said second rotation limitation point.

9. The brace of claim 7 wherein said rotation lock point is between said first and second rotation limitation points.

10. The brace of claim 7 wherein said first rotation arm has a first rotation plate positioned at an end of said first rotation arm and said second rotation arm has a second rotation plate positioned at an end of said second rotation arm.

11. An orthopedic brace comprising:
a first rotation plate;
a first rotation arm fixably connected to said first rotation plate;
a second rotation plate;
a second rotation arm fixably connected to said second rotation plate;
a pivotal connector connecting said first and second rotation plates and enabling rotational displacement of said first rotation plate and rotation arm relative to said second rotation plate and rotation arm about said pivotal connector in a first rotation direction or a second rotation direction opposite said first rotation direction;
a first rotation limiter selectively positionable with respect to said first rotation plate at a first rotation limitation point and engageable with said second rotation plate when said second rotation plate and rotation arm are rotated about said pivotal connector in said first rotation direction toward said first rotation limitation point, said first rotation limiter substantially preventing further rotation of said second rotation plate in said first rotation direction past said first rotation limiter at said first rotation limitation point when said second rotation plate engages said first rotation limiter while substantially permitting rotation of said second rotation plate in said second rotation direction;

a second rotation limiter selectively positionable with respect to said first rotation plate at a second rotation limitation point spaced a rotation distance apart from said first rotation limitation point and engageable with said second rotation plate when said second rotation plate and rotation arm are rotated about said pivotal connector in said second rotation direction toward said second rotation limitation point, said second rotation limiter substantially preventing further rotation of said second rotation plate in said second rotation direction past said second rotation limiter at said second rotation limitation point when said second rotation plate engages said second rotation limiter while substantially permitting rotation of said second rotation plate in said first rotation direction, said first and second rotation limiters in combination defining a limited rotation range of said first rotation plate and rotation arm relative to said second rotation plate and rotation arm about said pivotal connector in said first and second rotation directions between said first and second rotation limitation points; and a rotation lock member selectively positionable at a rotation lock point on one of said first and second rotation plates to achieve a rotation locked position substantially locking said first rotation plate and rotation arm against rotation relative to said second rotation plate and rotation arm in said first and second rotation directions.

12. The brace of claim 11 wherein said rotation lock member is selectively positioned at said rotation lock point while maintaining said first rotation limiter at said first rotation limitation point and maintaining said second rotation limiter at said second rotation limitation point.

13. The brace of claim 11 wherein said rotation lock point is between said first and second rotation limitation points.

14. A method for setting a rotation limit on a hinge for an orthopedic brace and for transitioning the hinge between a rotation locked position to lock the hinge against rotation and a rotation unlocked position to permit rotation of the hinge within the rotation limit, the method comprising:

providing a first rotation arm, a second rotation arm, a pivot enabling rotational displacement of said first and second rotation arms relative to one another about said pivot in a first rotation direction or a second rotation direction opposite said first rotation direction, a first rotation limiter and a second rotation limiter;

selectively positioning said first rotation limiter at a first rotation limitation point to prevent rotation of said second rotation arm about said pivot in said first rotation direction past said first rotation limiter while substantially permitting rotation of said second rotation plate in said second rotation direction;

selectively positioning said second rotation limiter at a second rotation limitation point to prevent rotation of said second rotation arm about said pivot in said second rotation direction past said second rotation limiter while substantially permitting rotation of said second rotation plate in said first rotation direction such that said first and second rotation limiters in combination define a limited rotation range of said first and second rotation arms relative to one another about said pivot in said first and second rotation directions between said first and second rotation limitation points; and selectively positioning a rotation lock member at a rotation lock point to achieve a rotation locked position substantially locking said first and second rotation arms against rotation relative to one another in said first and second rotation directions.

15. The method of claim 14 wherein said rotation lock member is selectively positioned at said rotation lock point while maintaining said first rotation limiter at said first rotation limitation point and maintaining said second rotation limiter at said second rotation limitation point.

16. The method of claim 14 wherein said rotation lock point is between said first and second rotation limitation points.

17. An orthopedic brace comprising:

a first rotation arm comprising a first arm member slidably engaged on a second arm member;

a second rotation arm comprising a third arm member slidably engaged on a fourth arm member;

a pivot enabling rotational displacement of said first and second rotation arms relative to one another about said pivot in a first rotation direction or a second rotation direction opposite said first rotation direction;

a first rotation limiter selectively positionable with respect to one of said first and second rotation arms to prevent rotation of said second rotation arm about said pivot in said first rotation direction past a first rotation limitation point while substantially permitting rotation of said second rotation plate in said second rotation direction;

a second rotation limiter selectively positionable with respect to one of said first and second rotation arms to prevent rotation of said second rotation arm about said pivot in said second rotation direction past a second rotation limitation point while substantially permitting rotation of said second rotation plate in said first rotation direction, said first and second rotation limiters in combination defining a limited rotation range of said first and second rotation arms relative to one another about said pivot in said first and second rotation directions between said first and second rotation limitation points;

a rotation lock member selectively positionable at a rotation lock point to achieve a rotation locked position substantially locking said first and second rotation arms against rotation relative to one another in said first and second rotation directions;

a first sliding lock member mounted on said first arm member and engageable with said second arm member to lock said second arm member from sliding relative to said first arm member; and a second sliding lock member mounted on said third arm member and engageable with said fourth arm member to lock said fourth arm member from sliding relative to said third arm member.

* * * * *